(12) United States Patent
Abdur-Rashid

(10) Patent No.: US 7,291,753 B2
(45) Date of Patent: Nov. 6, 2007

(54) TRANSFER HYDROGENATION PROCESSES AND CATALYSTS

(76) Inventor: Kamaluddin Abdur-Rashid, 3816 Morning Star Dr., Mississauga, Ontario (CA) L4T 1Y9

( * ) Notice: Subject to any disclaimer, the term of this patent is extended or adjusted under 35 U.S.C. 154(b) by 215 days.

(21) Appl. No.: 10/985,058

(22) Filed: Nov. 10, 2004

(65) Prior Publication Data

US 2005/0107638 A1    May 19, 2005

Related U.S. Application Data

(63) Continuation-in-part of application No. PCT/CA2004/000655, filed on May 3, 2004.

(60) Provisional application No. 60/467,137, filed on May 2, 2003.

(51) Int. Cl.
*C07C 209/00*   (2006.01)

(52) U.S. Cl. ............... 564/489; 546/329; 546/339; 548/570; 548/571; 568/881

(58) Field of Classification Search ............... 564/489; 546/329, 339; 548/570, 571; 568/881
See application file for complete search history.

(56) References Cited

U.S. PATENT DOCUMENTS

| | | |
|---|---|---|
| 4,322,306 A | 3/1982 | Dill |
| 4,387,087 A | 6/1983 | Deutsch et al. |
| 5,202,493 A | 4/1993 | Burk |
| 5,258,553 A | 11/1993 | Burk |
| 5,690,956 A | 11/1997 | Lau |
| 5,767,276 A | 6/1998 | Zhang |
| 6,184,381 B1 | 2/2001 | Ikariya et al. |
| 6,270,745 B1 | 8/2001 | Duatti et al. |
| 6,372,931 B1 | 4/2002 | Blacker et al. |
| 6,509,467 B1 | 1/2003 | Blacker et al. |
| 2002/0048549 A1 | 4/2002 | Duatti et al. |
| 2003/0144137 A1 | 7/2003 | Zhang et al. |
| 2004/0018147 A1 | 1/2004 | Duatti et al. |

FOREIGN PATENT DOCUMENTS

| | | |
|---|---|---|
| CA | 1107947 | 9/1981 |
| CA | 1177091 | 10/1984 |
| CA | 2108160 | 11/1992 |
| WO | WO97/13763 | 4/1997 |

(Continued)

OTHER PUBLICATIONS

Rahman et al., Coordination Chemistry and Catalytic Activity of Ruthenium Complexes of Terdentate Phosphorus-Nitrogen-Phosphorus (PNP) and Bidentate Phosphorus-Nitrogen (PNH) Ligands, Organometallics, 21 (23), 4927 -4933, 2002.*

(Continued)

*Primary Examiner*—Johann Richter
*Assistant Examiner*—Chukwuma Nwaonicha
(74) *Attorney, Agent, or Firm*—Bereskin & Parr

(57) ABSTRACT

The invention relates to a process for the reduction of compounds comprising a carbon-carbon (C=C), carbon-oxygen (C=O), or carbon-nitrogen (C=N) double bond, to a corresponding hydrogenated alkane, alcohol or amine, comprising contacting a compound comprising the C=C, C=O or C=N double bond with a hydrogen donor solvent and a catalyst comprising a metal complex having a tridentate aminodiphosphine ligand under transfer hydrogenation conditions.

64 Claims, 1 Drawing Sheet

FOREIGN PATENT DOCUMENTS

| | | |
|---|---|---|
| WO | WO98/25939 | 6/1998 |
| WO | WO02/08169 A1 | 1/2002 |
| WO | WO03/042135 A2 | 5/2003 |
| WO | WO03/053891 A1 | 7/2003 |
| WO | WO03/097571 A1 | 11/2003 |

OTHER PUBLICATIONS

Bianchini et al., Synthesis of the New Chiral Aminodiphosphine Ligands (R)- and (S)-(alpha-Methylbenzyl)bis(2-(diphenylphosphino)ethyl)amine and Their Use in the Enantioselective Reduction of alpha, beta-Unsaturated Ketones to Allylic Alcohols by Iridium Catalysis, Organometallics; 1995; 14(3); 1489-1502.*

Bianchini et al., Asymmetric hydrogen-transfer reduction of prochiral and a, b-unsaturated ketones by iridium complexes containing optically pure aminodiphosphine ligands, Journal of Molecular Catalysis A: Chemical (1998), 131(1), 13-19.*

Abdur-Rashid et al., Ruthenium Dihydride RuH2(PPh3)2((R,R)-cyclohexyldiamine) and Ruthenium Monohydride RuHCl(PPh3)2((R,R)-cyclohexyldiamine): Active Catalyst and Catalyst Precursor for the Hydrogenation of Ketones and Imines, Organometallics; (Communication); 2000; 19(14); 2655-2657.*

Abdur-Rashid et al., Catalytic Cycle for the Asymmetric Hydrogenation of Prochiral Ketones to Chiral Alcohols: Direct Hydride and Proton Transfer from Chiral Catalysts trans-Ru(H)2(diphosphine)(diamine) to Ketones and Direct Addition of Dihydrogen to the Resulting Hydridoamido Complexes, Organometallics, 20 (6), 7473-7474, 2001.*

Rahman et al., {Coordination Chemistry and Catalytic Activity of Ruthenium Complexes of Terdentate Phosphorus-Nitrogen-Phosphorus (PNP) and Bidentate Phosphorus-Nitrogen (PNH) Ligands, Organometallics, 21 (23), 4927 -4933, 2002}.*

Abdur-Rashid, K., et al. "RuHCl (diphosphine)(diamine): Catalyst precursors for the steroselective hydrogenation of ketones and imines", Organometallics, 2001, pp. 1047-1049, vol. 20.

Rahman, Mohammed S., et al., "Coordination Chemistry and Catalytic Activity of Ruthenium Complexes of Terdentate Phosphorus-Nitrogen-Phosphorus (PNP) and Bidentate Phosphorus-Nitrogen (PNH) Ligands", Organometallics, 2002, pp. 4927-4933, vol. 21, No. 23.

Nawar, Nagwa, "New rhodium-ruthenium heterobimetallic complexes with bridging bi- tri-dentate phosphine ligands", Journal of Organometallic Chemistry, 1999, pp. 217-221, vol. 590.

Morassi, R., et al., "Five-Coordination in Iron(II), Cobalt(II) and Nickel(II) Complexes", Coordination Chemistry Reviews, 1973, pp. 343-402, vol. 11.

Bianchini, Claudio et al., "Synthesis of the New Chiral Aminodiphosphine Ligands (R)- and (S)-(α-Methylbenzyl)bis(2-(diphenylphosphino)ethyl)amine and Their Use in the Enantioselective Reduction of α,β-Unsaturated Ketones to Allylic Alcohols by Iridium Catalysis", Organometallics, 1995, pp. 1489-1502, vol. 14, No. 3.

Jiang, Qiongzhong et al., "Synthesis of (1R, 1R')-2,6-Bis(1-diphenylphosphino)ethyl)pyridine and its Application in Asymmetric Transfer Hydrogenation", Tetrahedron Letters, 1996, pp. 797-800, vol. 37, No. 6.

Bianchini, Claudio et al., "Synthesis of the New Chiral (R)- and (S)-Aminodiphosphine Ligands sec-Butylbis(2-(diphenylphosphino)ethyl)amine, sec-Butylbis(2-(dicyclohexylphosphino)ethyl)amine, and (α-Methylbenzyl)bis(2-(dicyclohexylphosphino)ethyl)amine and Their Organometallic Chemistry When Combined with Iridium", Organometallics, 1997, pp. 4403-4414, vol. 16, No. 20.

STN Columbus, 1988-Present, vol. 140, Iss. 21 (20040521/ED).

STN Columbus 1907—Apr. 30, 2004, Vo. 140, Iss. 19 (20040430/ED).

STN Columbus, Apr. 30, 2004, Highest RN 678535-01-8.

Burk, Mark J. et al., "New Chiral Phospholanes; Synthesis, Characterization, and Use in Asymmetric Hydrogenation Reactions", Tetrahedron: Asymmetry, 1991, pp. 569-592, vol. 2, No. 7.

Bianchini, Claudio et al., "Asymmetric hydrogen-transfer reduction of prochiral and α, β-unsaturated ketones by iridium complexes containing optically pure aminodiphosphine ligands", Journal of Molecular Catalysis A: Chemical, 1998, pp. 13-19, vol. 132.

Khan, M. M. Taqui et al., "Synthesis and Characterization of Novel Platinum Group Metal Complexes of Bis[2-(diphenylphosphino)ethyl]amine", Polyhedron, 1987, pp. 1727-1735, vol. 6, No. 9.

Khan, M. M. Taqui et al., "Homogeneous Hydrogenation of Cyclohexene Catalyzed by Complexes of Rhodium and Iridium" Journal of Molecular Catalysis, 1984, pp. 207-217, vol. 26.

Khan, M. M. Taqui et al., "Homoegeneous Hydrogenation of Cyclohexene Catalyzed by Ru(II) and (III) and Their Trichlorostannato Complexes: Proton NMR and Rate Studies", Journal of Molecular Catalysis, 1987, pp. 161-171, vol. 42.

* cited by examiner

TRANSFER HYDROGENATION PROCESSES AND CATALYSTS

FIELD OF THE INVENTION

The present invention relates to the field of catalytic transfer hydrogenation, in which a catalytic system comprising a metal complex containing a tridentate aminodiphosphine ligand and a hydrogen donor solvent is used for the reduction of compounds containing a carbon-carbon (C=C) or a carbon-heteroatom (C=O, C=N) double bond. In particular, this invention relates to the process of making optically active compounds.

BACKGROUND OF THE INVENTION

Catalytic hydrogenation is one of the fundamental reactions in chemistry, and is used in a large number of chemical processes. It is now recognized that catalytic hydrogenations of carbon-carbon double bonds of alkenes, and carbon-heteroatom double bonds of ketones, aldehydes and imines are indispensable processes for the production of the wide range of alkanes, alcohols and amines, including chiral compounds, which are useful as valuable end products and precursors for the pharmaceutical, agrochemical, flavor, fragrance, material and fine chemical industries.

Amongst the several different kinds of processes known to achieve such transformations, two important types are: (a) transfer hydrogenation processes, in which hydrogen-donors such as secondary alcohols, and in particular isopropanol ($^i$PrOH), and triethylammonium formate (HCOOH/NEt$_3$) are used, and (b) hydrogenation processes, in which molecular hydrogen is used. Both hydrogen transfer and hydrogenation processes need a catalyst or catalytic system to activate the reducing agent, such as an alcohol, HCOOH/NEt$_3$ or molecular hydrogen.

The catalytic hydrogenation processes developed by Noyori and coworkers (Ohkuma et al., *J. Am. Chem. Soc.*, 1995, 107, 2675 and 10417) are very attractive, since the catalysts consist of air-stable ruthenium complexes of the type RuCl$_2$(PR$_3$)$_2$(diamine) and RuCl$_2$(diphosphine)(diamine) which are precursors for the generation of what appears to be some of the most active catalysts for the homogeneous and asymmetric hydrogenation of ketones and imines in the presence of a base and hydrogen gas. It has been proposed and subsequently mechanistically elucidated that the key molecular recognition feature of these catalysts is the presence of mutually cis N—H and Ru—H moieties of the catalytic dihydride species (RuH$_2$(PR$_3$)$_2$(diamine) and RuH$_2$(diphosphine)(diamine)) that electronically bind and activate the substrate and facilitate reduction.

Transfer hydrogenation, whereby a hydrogen donor solvent such as 2-propanol or HCOOH/NEt$_3$ serves as the reducing agent, though currently not as highly developed as catalytic hydrogenation, is widely recognized as a potentially lucrative niche technology that is particularly significant and attractive whenever hydrogenation, for whatever reason, is not applicable or practical. Hence, transfer hydrogenation is complimentary to hydrogenation processes, especially for small to medium scale transformations. In most cases, 2-propanol is the conventional hydrogen donor solvent of choice because it is stable, non-toxic, has a moderate boiling point (82° C.), is readily available, inexpensive and environmentally friendly.

Amongst the potentially interesting transfer hydrogenation catalysts reported in the prior art to activate 2-propanol, there are ruthenium complexes with tetradentate diamine-diphosphine ligands, (Gao et al. in Tianranqi Huagong, 1995, 20, 1 or CN 1047597 B) and the analogous ruthenium complexes with tetradentate diiminediphosphine ligands, (Xu et al. in Yingyong Huaxue 1997, 14, 58 or Gao et al. in Chirality, 2000, 12, 383). The reported processes, using these two types of complexes, relate to their use for the reduction of carbon-oxygen double bonds, such as those found in ketones and aldehydes.

Noyori and coworkers have also described an efficient catalyst system. generated from the complex Ru($\eta^6$-arene)(tosyldiamine)Cl for the asymmetric hydrogenation of ketones and imines by transferring hydrogen from triethylammonium formate (Noyori et al., *Acc. Chem. Res.* 1997, 30, 97-102). More recently, Blacker et al. demonstrated that cyclopentadienylrhodium and areneruthenium complexes in the presence of tosylated diamines and aminoalcohols are very efficient catalysts for the transfer hydrogenation of a wide range of ketones, imines and iminium salts under mild reaction conditions (A. J. Blacker et al., U.S. Pat. No. 6,372,931 B1, 2002; U.S. Pat. No. 6,509,467 B1, 2003).

There are some reports in the literature of the preparation of tridentate aminodiphosphine ligands and their transition metal complexes, including the use of some of these complexes for hydrogenation reactions, involving the use of hydrogen gas as the reducing agent (M. J. Burk et al., *Tetrahedron: Asymmetry*, 1991, 2, 569; M. J. Burk et al., U.S. Pat. No. 5,258,553, 1993; M. M. Taqui Khan et al., *J. Mol. Catal.*, 1987, 42, 161; M. M. Taqui Khan et al., *Polyhedron*, 1987, 6, 1727). None of these reports describes processes in which such complexes are used for transfer hydrogenation processes, involving a hydrogen donor solvent as the reducing agent.

SUMMARY OF THE INVENTION

It has now been found that metal complexes comprising tridentate aminodiphosphine ligands are particularly efficient catalysts for the reduction of carbon-carbon and carbon-heteroatom double bonds under transfer hydrogenation conditions.

Therefore, the present invention includes a process for the reduction of compounds comprising a carbon-carbon (C=C), carbon-oxygen (C=O) or carbon-nitrogen (C=N) double bond, to a corresponding hydrogenated alkane, alcohol or amine, comprising contacting a compound comprising the C=C, C=O or C=N double bond with a hydrogen donor and a catalyst comprising a metal complex having a tridentate aminodiphosphine ligand under transfer hydrogenation conditions.

In an embodiment of the invention, the compound comprising a carbon-carbon (C=C), carbon-oxygen (C=O) or carbon-nitrogen (C=N) double bond is a compound of formula (I):

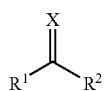

(I)

wherein,
X is selected from the group consisting of CR$^3$R$^4$, NR$^5$, (NR$^5$R$^6$)$^+$Q$^-$ and O;
R$^1$ and R$^2$ each simultaneously or independently are selected from the group consisting of H, aryl, C$_{1-20}$alkyl, C$_{2-20}$alkenyl, C$_{3-20}$cycloalkyl and heteroaryl, said latter 5 groups being optionally substituted, or $R^1$ and $R^2$ are linked to form an optionally substituted ring;

$R^3$ to $R^6$ each independently or simultaneously are selected from the group consisting of H, OH, $C_{1-20}$alkoxy, aryloxy, $C_{1-20}$alkyl, $C_{2-20}$alkenyl, $C_{3-20}$cycloalkyl and aryl, said latter 6 groups being optionally substituted, or one or more of $R^1$ to $R^6$ are linked to form an optionally substituted ring or rings; and $Q^-$ represents an anion, wherein heteroaryl is a mono- or bicyclic heteroaromatic radical containing from 5 to 10 atoms, of which 1-3 atoms may be a heteroatom selected from the group consisting of S, O and N, and wherein the optional substituents are selected from the group consisting of halo, OH, $NH_2$, $OR^c$, $NR^c_2$ or $R^c$ groups, in which $R^c$ is selected from the group consisting of $C_{1-6}$alkyl, $C_{2-6}$alkenyl and aryl and one or more of the carbon atoms in the alkyl, alkenyl and cycloalkyl groups may be optionally replaced with a heteroatom selected from the group consisting of O, S, N, P and Si.

Reduction of compounds of formula I using the process of the invention provides the corresponding hydrogenated compounds of formula (I'):

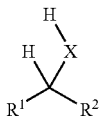

(I')

wherein X, $R^1$ and $R^2$ are defined as in formula (I).

In one embodiment, the processes of the invention are characterized by the use of a catalytic system comprising a metal complex with a tridentate aminodiphosphine ligand, with or without a base, in which the metal complex is of the formula $$[M(P_2NH)Y_m]$$ (II)

wherein

M is a metal;

Y simultaneously or independently are any anionic or neutral ligand;

m is an integer representing the number of ligands Y that are required to fulfill the valency requirements of M; and ($P_2NH$) represents a tridentate aminodiphosphine ligand of formula (III):

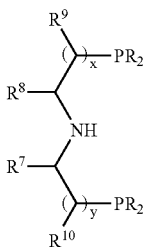

(III)

in which $R^7$ to $R^{10}$ simultaneously or independently are selected from the group consisting of H, $C_{1-20}$alkyl, $C_{2-20}$alkenyl, $C_{3-20}$cycloalkyl and aryl, said latter 4 groups being optionally substituted, or two adjacent or geminal groups are bonded together to form an optionally substituted ring;

x and y are, simultaneously or independently, equal to 0, 1, 2, 3 or 4; and

R is simultaneously or independently selected from the group consisting of H, $C_{1-20}$alkyl, aryl and $C_{2-20}$alkenyl, OR and $NR_2$, said latter 5 groups being optionally substituted, or the R groups on the same P atom may be linked together to form an optionally substituted monocyclic or polycyclic, saturated, unsaturated and/or aromatic ring system having 4 or more atoms, including the phosphorous atom to which said R groups are bonded, and in which one or more carbon atoms in said monocyclic or polycyclic ring system may optionally be replaced with a heteroatom selected from O, S, N, and Si, wherein the optional substituents are selected from one or more of halo, OH, $NH_2$, $OR^c$, $NR^c_2$ and $R^c$, in which $R^c$ is selected from the group consisting of $C_{1-6}$alkyl; $C_{2-6}$alkenyl and aryl.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in greater detail with reference to the following drawings in which.

DETAILED DESCRIPTION OF THE INVENTION

Figure 1:
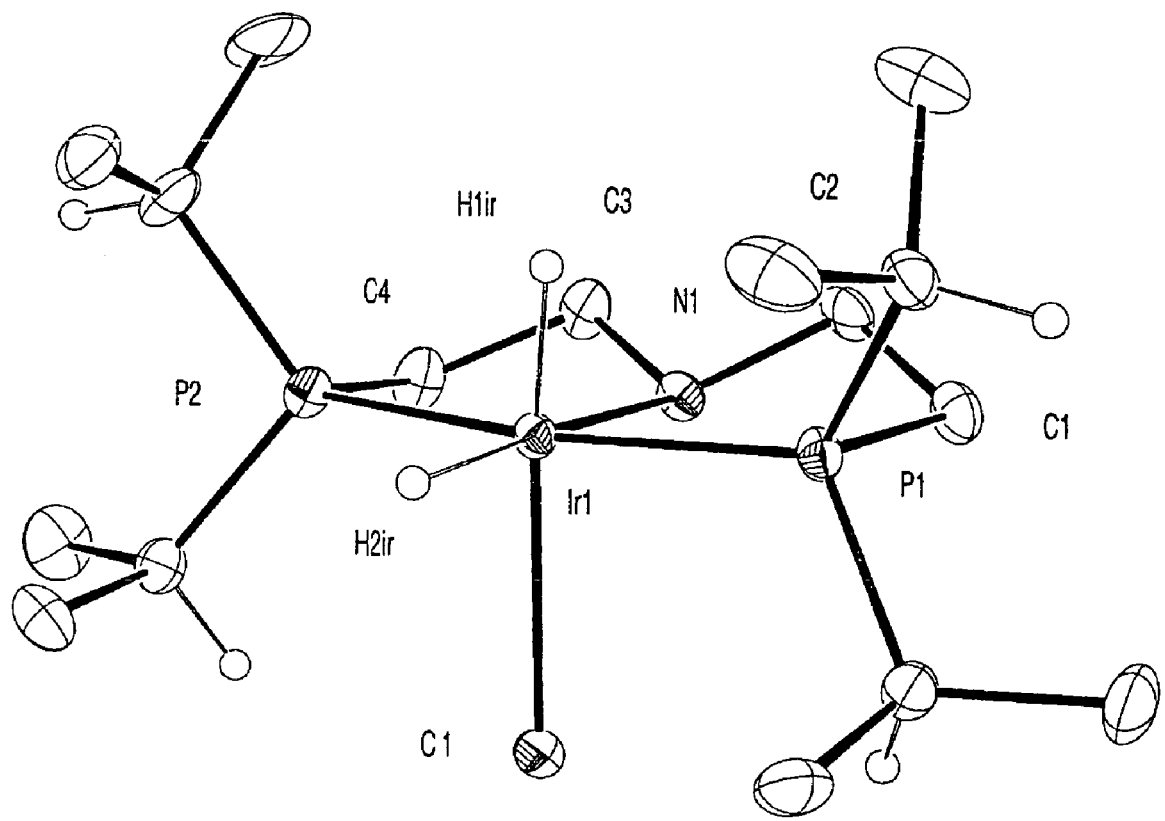
FIG. 1 shows an x-ray structure of the complex $IrH_2Cl$ [($^iPr_2PC_2H_4)_2NH$].

It has been found that tridentate aminodiphosphine ligands, when complexed with a metal, are particularly efficient catalysts for the reduction of C=C, C=O and C=N double bonds under transfer hydrogenation conditions.

Accordingly, the present invention relates to a process for the reduction of compounds comprising a carbon-carbon (C=C), carbon-oxygen (C=O) or carbon-nitrogen (C=N) double bond, to a corresponding hydrogenated alkane, alcohol or amine, comprising contacting a compound comprising the C=C, C=O or C=N double bond with a hydrogen donor and a catalyst comprising a metal complex having a tridentate aminodiphosphine ligand under transfer hydrogenation conditions.

The compound comprising a C=C, C=O or C=N, includes compounds having one or more C=C, C=O and/or C=N bonds.

In an embodiment of the invention, the compound comprising a carbon-carbon (C=C), carbon-oxygen (C=O) or carbon-nitrogen (C=N) double bond is a compound of formula (I):

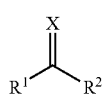

(I)

wherein,

X is selected from the group consisting of $CR^3R^4$, $NR^5$, $(NR^5R^6)^+Q^-$ and O;

$R^1$ and $R^2$ each simultaneously or independently are selected from the group consisting of H, aryl, $C_{1-20}$alkyl, $C_{2-20}$alkenyl, $C_{3-20}$cycloalkyl and heteroaryl, said latter 5 groups being optionally substituted, or $R^1$ and $R^2$ are linked to form an optionally substituted ring;

$R^3$ to $R^6$ each independently or simultaneously are selected from the group consisting of H, OH, $C_{1-20}$alkoxy, aryloxy, $C_{1-20}$alkyl, $C_{2-20}$alkenyl, $C_{3-20}$cycloalkyl and aryl, said latter 6 groups being optionally substituted, or one or more of $R^1$ to $R^6$ are linked to form an optionally substituted ring or rings; and $Q^-$ represents an anion, wherein heteroaryl is a mono- or bicyclic heteroaromatic radical containing from 5 to 10 atoms, of which 1-3 atoms may be a heteroatom selected from the group consisting of S, O and N, and wherein the optional substituents are selected from the group consisting of halo, OH, $NH_2$, $OR^c$, $NR^c_2$ or $R^c$ groups, in which $R^c$ is selected from the group consisting of $C_{1-6}$alkyl, $C_{2-6}$alkenyl and aryl, and one or more of the carbon atoms in the alkyl, alkenyl and cycloalkyl groups may be optionally replaced with a heteroatom selected from the group consisting of O, S, N, P and Si.

Reduction of compounds of formula I using the process of the invention provides the corresponding hydrogenated compounds of formula (I'):

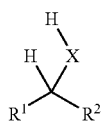

(I')

wherein X, $R^1$ and $R^2$ are defined as in formula (I).

Since $R^1$ and $R^2$ may be different, it is hereby understood that the final product, of formula (I'), may be chiral, thus possibly consisting of a practically pure enantiomer or of a mixture of stereoisomers, depending on the nature of the catalyst used in the process.

The term "$C_{1-n}$alkyl" as used herein means straight and/or branched chain alkyl radicals containing from one to "n" carbon atoms and includes methyl, ethyl, propyl, isopropyl, t-butyl, n-decyl and the like.

The term "$C_{1-n}$alkoxy" as used herein means straight and/or branched chain alkoxy radicals containing from one to "n" carbon atoms and includes methoxy, ethoxy, propyoxyl, isopropyloxy, t-butoxy, heptoxy and the like.

The term "aryl" as used herein means unsubstituted or substituted mono- or bicyclic aromatic radicals containing from 6 to 14 carbon atoms and includes phenyl and naphthyl and the like.

The term "heteroaryl" as used herein means unsubstituted or substituted mono- or bicyclic heteroaromatic radicals containing from 5 to 14 atoms, of which 1-3 atoms may be a heteroatom selected from the group consisting of S, O and N, and includes furanyl, thienyl, pyrrolo, pyridyl, indolo, benzofuranyl and the like.

The term "halo" as used herein means halogen and includes chloro, flouro, bromo, iodo and the like.

The term "$C_{2-n}$alkenyl" as used herein means straight and/or branched chain alkenyl groups containing from two to "n" carbon atoms and at least one double bond and includes allyl, isoprenyl and the like.

The term "$C_{3-20}$cycloalkyl" as used herein means a saturated carbocyclic group containing from three to twenty carbon atoms and includes cyclopropyl, cyclobutyl, cyclopentyl, cyclodecyl and the like.

The term "ring" or "ring system" as used herein refers to carbocycles, except where indicated that one or more carbon atoms may be replaced with heteroatom.

The processes of the invention are characterized by the use of a catalytic system comprising a metal complex with a tridentate aminodiphosphine ligand with or without a base. In one embodiment, the metal complex is of the formula

(II)

wherein

M is a metal;

Y simultaneously or independently are any anionic or neutral ligand;

m is an integer representing the number of ligands Y that are required to fulfill the valency requirements of M; and ($P_2NH$) represents a tridentate aminodiphosphine ligand of formula (III):

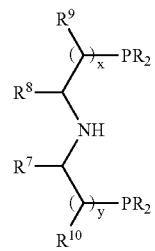

(III)

in which $R^7$ to $R^{10}$ simultaneously or independently are selected from the group consisting of H, $C_{1-20}$alkyl, $C_{2-20}$alkenyl, $C_{3-20}$cycloalkyl and aryl, said latter 4 groups being optionally substituted, or two adjacent or geminal groups are bonded together to form an optionally substituted ring;

x and y are, simultaneously or independently, equal to 0, 1, 2, 3 or 4; and

R is simultaneously or independently selected from the group consisting of H, $C_{1-20}$alkyl, aryl and $C_{2-20}$alkenyl, OR and $NR_2$, said latter 5 groups being optionally substituted, or the R groups on the same P atom may be linked together to form an optionally substituted monocyclic or polycyclic, saturated, unsaturated and/or aromatic ring system having 4 or more atoms, including the phosphorous atom to which said R groups are bonded, and in which one or more carbon atoms in said monocyclic or polycyclic ring system may optionally be replaced with a heteroatom selected from O, S, N, and Si, wherein the optional substituents are selected from one or more of halo, OH, $NH_2$, $OR^c$, $NR^c_2$ and $R^c$, in which $R^c$ is selected from the group consisting of $C_{1-6}$alkyl, $C_{2-6}$alkenyl and aryl.

In the present invention, the tridentate ligand of formula III includes those in which $R^7$ to $R^{10}$ simultaneously or independently are selected from the group consisting of H, $C_{1-20}$alkyl, $C_{2-20}$alkenyl, $C_{3-20}$cycloalkyl and aryl, said latter 4 groups being optionally substituted, or two adjacent or geminal groups are bonded together to form an optionally substituted ring. In an embodiment of the invention $R^7$ to $R^{10}$ simultaneously or independently are selected from the group consisting of H, $C_{1-10}$alkyl, $C_{2-10}$alkenyl, $C_{3-10}$cycloalkyl and aryl, said latter 4 groups being optionally substituted, or two adjacent or geminal groups are bonded together to form an optionally substituted ring. In further embodiments of the invention, $R^7$ to $R^{10}$ simultaneously or independently are selected from the group consisting of H, $C_{1-4}$alkyl, $C_{2-4}$alkenyl, $C_{3-6}$cycloalkyl and aryl, said latter 4 groups being optionally substituted, or two adjacent or geminal groups are bonded together to form an optionally substituted ring, said ring containing 6 atoms, including the carbons to which said groups are attached. In further embodiments of the invention $R^7$ to $R^{10}$ are all H.

In the present invention, the tridentate ligand of formula III further includes those in which x and y are, simultaneously or independently, equal to 0, 1, 2, 3 or 4. In embodiments of the invention, x and y are simultaneously equal to 0, 1, 2, 3 or 4. In further embodiments of the invention, x and y are simultaneously equal to 0, 1 or 2. In still further embodiments of the invention, x and y are simultaneously equal to 1.

In the present invention, the tridentate ligand of formula III still further includes those in which R is simultaneously or independently selected from the group consisting of H, $C_{1-20}$alkyl, aryl and $C_{2-20}$alkenyl, OR and $NR_2$, said latter 5 groups being optionally substituted, or the R groups on the same P atom may be linked together to form an optionally substituted monocyclic or polycyclic ring system having 4 or more atoms, including the phosphorous atom to which said R groups are bonded, in which the rings may be saturated, unsaturated and/or aromatic and in which one or more carbon atoms in said monocyclic or polycyclic ring system may optionally be replaced with a heteroatom selected from O, S, N, and Si. In an embodiment of the invention, R is simultaneously or independently selected from the group consisting of H, $C_{1-10}$alkyl, aryl and $C_{2-10}$alkenyl, said latter 3 groups being optionally substituted, or the R groups on the same P atom may be linked together to form an optionally substituted monocyclic or polycyclic ring system having 4 or more atoms, including the phosphorous atom to which said R groups are bonded, in which the rings may be saturated, unsaturated and/or aromatic and in which one or more carbon atoms in said monocyclic or polycyclic ring system may optionally be replaced with a heteroatom selected from O and NH. In still further embodiments of the invention, R is simultaneously or independently selected from the group consisting of H, $C_{1-6}$alkyl, phenyl, naphthyl and $C_{2-6}$alkenyl, said latter 3 groups being optionally substituted, or the R groups on the same P atom may be linked together to form an optionally substituted monocyclic, fused bicylic, fused tricyclic, fused quadracyclic or fused pentacyclic ring system having 4-23 atoms, including the phosphorous atom to which said R groups are bonded, in which the rings may be saturated, unsaturated and/or aromatic and in which one or more carbon atoms in said monocyclic or polycyclic ring system may optionally be replaced with a heteroatom selected from O and NH.

In an embodiment of the invention, R is simultaneously $C_{1-6}$alkyl or phenyl, in particular, methyl, ethyl, propyl, isopropyl, t-butyl, sec-butyl or phenyl.

In another embodiment of the invention, the two R groups on each phosphorus atom are linked to form a monocyclic saturated ring contain from 4 to 7 atoms, specifically 4-5 atoms, including the phosphorus atom to which the R groups are attached, said ring being optionally substituted with 1 to 2 substituents independently selected from $C_{1-6}$alkyl, $C_{2-6}$alkenyl and aryl, specifically $C_{1-4}$alkyl, $C_{2-4}$alkenyl and phenyl, more specifically methyl or phenyl, and wherein one or two of the carbon atoms in the ring may be replaced with a heteroatom selected from O, S and N—$C_{1-4}$alkyl, specifically O and N—$CH_3$. It is a further embodiment of the invention, that when the two R groups on each phosphorus atom are linked to form a monocyclic ring, any optional heteroatoms or optional substituents are located at the positions alpha to the phosphorus atom.

In yet another embodiment of the present invention, the two R groups on the phosphorus atom are linked to form a polycyclic ring system comprising 3, 5 or 7 rings each which may be fully saturated, partially unsaturated and/or aromatic and which are optionally substituted with 1 to 2 substituents independently selected from $C_{1-6}$alkyl, $C_{2-6}$alkenyl and aryl, specifically $C_{1-4}$alkyl, $C_{2-4}$alkenyl and phenyl, more specifically methyl or phenyl, and wherein one or two of the carbon atoms in the ring may be replaced with a heteroatom selected from O, S and N—$C_{1-4}$alkyl, specifically O and N—$CH_3$. It is a further embodiment of the invention, that when the two R groups on each phosphorus atom are linked to form a polycyclic ring system, any optional heteroatoms or optional substituents are located at the positions alpha to the phosphorus atom.

Further it is an embodiment of the invention that both phosphorus atoms in the compounds of Formula II are identically substituted.

According to the invention, the optional substituents on the compounds of formula III are selected from one or more of halo, OH, $NH_2$, $OR^c$, $NR^c_2$ and $R^c$, in which $R^c$ is selected from the group consisting of $C_{1-6}$alkyl, $C_{2-6}$alkenyl and aryl. In embodiments of the invention, the optional substituents are selected from one or more of halo, OH, $NH_2$, $OR^c$, $NR^c_2$ and $R^c$, in which $R^c$ is selected from the group consisting of $C_{1-4}$alkyl, $C_{2-4}$alkenyl and phenyl, specifically methyl and phenyl.

The processes of the invention are particularly attractive when the aminodiphosphine ligand ($P_2NH$) of formula (III) is chiral. Whenever ($P_2NH$) is chiral, the process of the invention can be useful in asymmetric transfer hydrogenation.

In embodiments of the present invention, the ligand ($P_2NH$) is selected from one of the formulae III(a)-III(g) below:

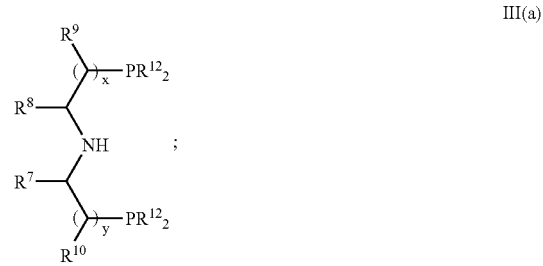

III(a)

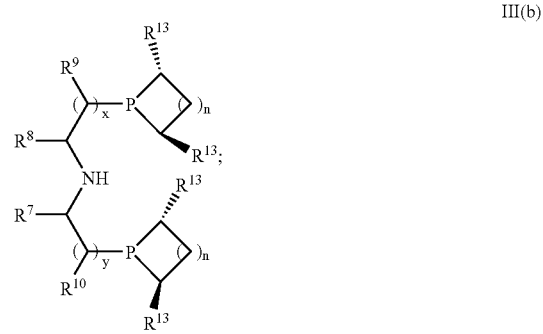

III(b)

-continued

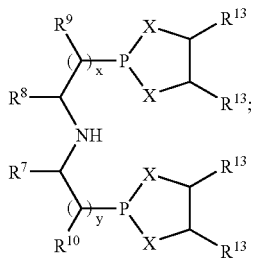

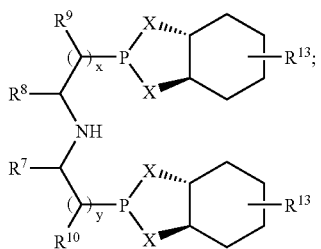

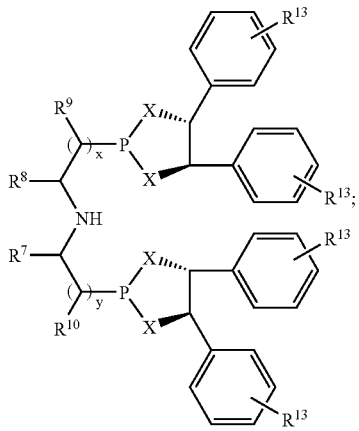

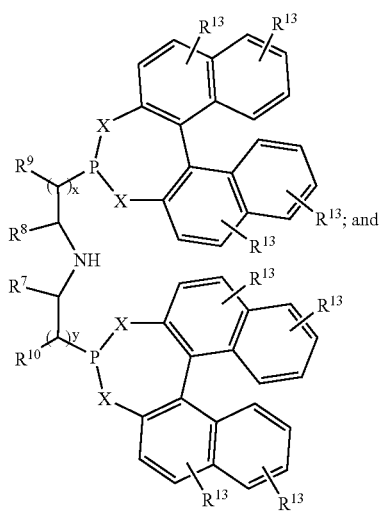

-continued

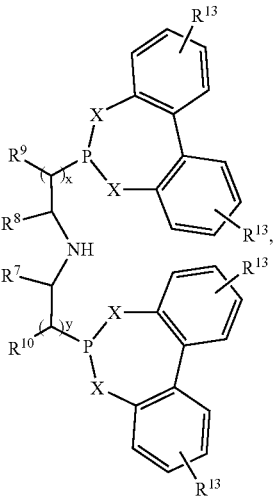

wherein

R$^7$ to R$^{10}$ simultaneously or independently are selected from the group consisting of H. C$_{1-20}$alkyl, C$_{2-20}$alkenyl, C$_{3-20}$cycloalkyl and aryl, said latter 4 groups being optionally substituted, or two adjacent or geminal groups are bonded together to form an optionally substituted ring;

R$^{12}$ simultaneously or independently are selected from the group consisting of halo, OH, NH$_2$, OR$^c$, NR$^c_2$ and R$^c$;

R$^{13}$ simultaneously or independently are selected from the group consisting of H, halo, OH, NH$_2$, OR$^c$, NR$^c_2$ and R$^c$;

R$^c$ simultaneously or independently are selected from the group consisting of C$_{1-6}$alkyl, C$_{2-6}$alkenyl and aryl;

x and y simultaneously or independently are integers selected from the group consisting of 0, 1, 2, 3, and 4;

n is an integer selected from the group consisting of 1, 2, 3 and 4; and

X simultaneously or independently are CH$_2$, O, NH or NR$^c$.

In embodiments of the invention, the ligand P$_2$NH is a compound of formula III(a) and R$^7$ to R$^{10}$ simultaneously or independently are selected from the group consisting of H, C$_{1-6}$alkyl, C$_{2-6}$alkenyl, C$_{3-6}$cycloalkyl and aryl, x and y simultaneously or independently are selected from the group consisting of 1, 2 and 3 and R$^{12}$ is R$^c$, in which R$^c$ is selected from the group consisting of C$_{1-6}$alkyl, C$_{2-6}$alkenyl and phenyl. In further embodiments of the invention P$_2$NH is a compound of formula III(a) and R$^7$ to R$^{10}$ simultaneously or independently are selected from the group consisting of H, methyl and phenyl, specifically H, x and y simultaneously or independently are selected from the group consisting of 1 and 2, specifically 1, and R$^{12}$ is R$^c$, in which R$^c$ is selected from the group consisting of C$_{1-4}$alkyl and phenyl, specifically i-propyl and phenyl.

In embodiments of the invention, the ligand P$_2$NH is a compound of formula III(b) and R$^7$ to R$^{10}$ simultaneously or independently are selected from the group consisting of H, C$_{1-6}$alkyl, C$_{2-6}$alkenyl, C$_{3-6}$cycloalkyl and aryl, x and y simultaneously or independently are selected from the group consisting of 1, 2 and 3, R$^{13}$ is R$^c$, in which R$^c$ is C$_{1-6}$alkyl and n is 1 to 3. In further embodiments of the invention P$_2$NH is a compound of formula III(b) and R$^7$ to R$^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and n is 1 or 2, specifically 1.

In embodiments of the invention, the ligand $P_2NH$ is a compound of formula III(c) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl. In further embodiments of the invention $P_2NH$ is a compound of formula III(c) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

In embodiments of the invention, the ligand $P_2NH$ is a compound of formula III(d) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl. In further embodiments of the invention $P_2NH$ is a compound of formula III(d) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

In embodiments of the invention, the ligand $P_2NH$ is a compound of formula III(e) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl. In further embodiments of the invention $P_2NH$ is a compound of formula III(e) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

In embodiments of the invention, the ligand $P_2NH$ is a compound of formula III(f) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl. In further embodiments of the invention $P_2NH$ is a compound of formula III(f) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

In embodiments of the invention, the ligand $P_2NH$ is a compound of formula III(g) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl. In further embodiments of the invention $P_2NH$ is a compound of formula III(g) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

It is an embodiment of the invention that the ligand ($P_2NH$) is selected from a compound of the formula III(a), III(b) and III(f).

In the catalysts of formula II, the metal, M, is any transition metal of groups 3 through 12 of the periodic table, suitably groups 4 through 10, plus the lanthanides and actinides. Examples of suitable metals include, but are not limited to Co, Rh, Ir, Ru, Os and Re. In an embodiment of the invention, the M is Ir.

The ligand Y, may be a halide; alkyl; aryl; unsaturated hydrocarbyl including but not limited to olefin, diolefin such as cyclooctadiene or norbornadiene or alkyne; acetate; alkoxide; amide; hydride; sulfide; phosphine; carbon monoxide; amine; ether; hydroxide; oxo; imido; or acetylacetonate groups. When the complex has a negative charge, a countercation is required. Examples include ammonium, tetraalkylammonium, sodium, potassium or lithium. When the complex has a positive charge, a counteranion is required. Suitable examples of counteranions are tetrafluoroborate, hexafluoroantimonate or chloride.

In a general way, the complexes of formula (II) can be prepared and isolated prior to their use in the process according to the general methods described in the literature or using the methods described herein. Moreover, the complexes can be prepared in situ, by several methods, in the reaction medium, without isolation or purification, just before their use.

The catalytic system characterizing the process of the instant invention may comprise a base. Said base can be the substrate itself, if the latter is basic, or any conventional base. One can cite, as non-limiting examples, organic non-coordinating bases such as DBU, an alkaline or alkaline-earth metal carbonate, a carboxylate salt such as sodium or potassium acetate, or an alcoholate or hydroxide salt. In an embodiment of the invention, the bases are the alcoholate or hydroxide salts selected from the group consisting of the compounds of formula $(R^{14}O)_2M'$ and $R^{14}OM''$, wherein M' is an alkaline-earth metal, M'' is an alkaline metal and $R^{14}$ stands for hydrogen or a linear or branched alkyl group.

Standard transfer hydrogenation conditions, as used herein, typically implies the mixture of the substrate with a metal complex of formula (II) with or without a base, possibly in the presence of a solvent, and then treating such a mixture with a hydrogen donor solvent at a chosen pressure and temperature.

The complexes of formula (II) can be added to the reaction medium in a large range of concentrations. As non-limiting examples, one can cite as complex concentration values those ranging from 0.1 ppm to 50,000 ppm, relative to the amount of substrate, thus representing respectively a substrate/complex (S/com) ratio of $10^7$ to 20. In an embodiment of the invention, the complex concentration will be comprised between 0.1 and 1000 ppm, i.e. a S/com ratio of $10^7$ to 1000 respectively. In a further embodiment of the invention, there will be used concentrations in the range of 0.5 to 100 ppm, corresponding to a S/com ratio of 10,000 to $2 \times 10^6$ respectively.

If required, useful quantities of base, added to the reaction mixture, may be comprised in a relatively large range. One can cite, as non-limiting examples, ranges between 1 to 50,000 molar equivalents relative to the complex (e.g. base/com=0.5 to 50,000), or 100 to 20,000, or even between 400 and 10,000 molar equivalents. However, it should be noted that it is also possible to add a small amount of base (e.g. base/com=1 to 3) to achieve high yields.

In the processes of this invention, the transfer hydrogenation reaction can be carried out in the presence or absence of a solvent. When a solvent is required or used for practical reasons, then any solvent current in transfer hydrogenation reactions can be used for the purposes of the invention. Non-limiting examples include aromatic solvents such as benzene, toluene or xylene, hydrocarbon solvents such as hexane or cyclohexane, ethers such as tetrahydrofuran, or yet primary or secondary alcohols, or mixtures thereof. A person skilled in the art is well able to select the solvent most convenient in each case to optimize the transfer hydrogenation reaction.

Hydrogen donors include primary and secondary alcohols, primary and secondary amines, carboxylic acids and their esters and amine salts, readily dehydrogenatable hydrocarbons, clean reducing agents, and any combination thereof.

Primary and secondary alcohols which may be employed as hydrogen donors comprise commonly from 1 to 10 carbon atoms, specifically from 2 to 7 carbon atoms, and more specifically 3 or 4 carbon atoms. Examples of primary and secondary alcohols that may be represented as hydrogen donors include methanol, ethanol, propan-1-ol, propan-2-ol, butan-1-ol, butan-2-ol, cyclopentanol, cyclohexanol, benzylalcohol, and menthol. When the hydrogen donor is an alcohol, it is an embodiment of the invention that the alcohol is a secondary alcohols, for example propan-2-ol, and butan-2-ol.

Primary and secondary amines which may be employed as hydrogen donors comprise commonly from 1 to 20 carbon atoms, specifically from 2 to 14 carbon atoms, and more specifically 3 or 8 carbon atoms. Examples of primary and secondary amines, which may be represented as hydrogen donors, include ethylamine, propylamine, isopropylamine, butylamine, isobutylamine, hexylamine, diethylamine, dipropylamine, di-isopropylamine, dibutylamine, di-isobutylamine, dihexylamine, benzylamine, dibenzylamine and piperidine. When the hydrogen donor is an amine, it is an embodiment of the invention that the amine is a primary amines, for example primary amines comprising a secondary alkyl group, such as isopropylamine and isobutylamine.

Carboxylic acids or their esters, which may be employed as hydrogen donors, comprise commonly from 1 to 10 carbon atoms, specifically from 1 to 3 carbon atoms. In certain embodiments, the carboxylic acid is advantageously a beta-hydroxy-carboxylic acid. Esters may be derived from the carboxylic acid and a $C_{1-10}$ alcohol. Examples of carboxylic acids, which may be employed as hydrogen donors include formic acid, lactic acid, ascorbic acid and mandelic acid. When a carboxylic acid is employed as hydrogen donor, it is an embodiment that at least some of the carboxylic acid is present as an amine salt or ammonium salt. Amines, which may be used to form such salts, include both aromatic and non-aromatic amines, also primary, secondary and tertiary amines and comprise typically from 1 to 20 carbon atoms. In an embodiment of the invention the amine is a tertiary amine, for example trialkylamines. Examples of amines, which may be used to form salts, include trimethylamine, triethylamine, di-isopropylethylamine and pyridine. In a further embodiment of the invention, the amine is triethylamine. When at least some of the carboxylic acid is present as an amine salt, particularly when a mixture of formic acid and triethylamine is employed, the mole ratio of acid to amine is commonly about 5:2. This ratio may be maintained during the course of the reaction by the addition of either component, but usually by the addition of the carboxylic acid.

Readily dehydrogenatable hydrocarbons, which may be employed as hydrogen donors, comprise hydrocarbons, which have a propensity to aromatise or hydrocarbons, which have a propensity to form highly conjugated systems. Examples of readily dehydrogenatable hydrocarbons, which may be employed as hydrogen donors, include cyclohexadiene, cyclohexane, tetralin, dihydrofuran and terpenes.

Clean reducing agents which may be represented as hydrogen donors comprise reducing agents with a high reduction potential, particularly those having a reduction potential relative to the standard hydrogen electrode far greater than about $-0.1$ eV, often greater that about $-0.5$ eV, and preferably greater than about $-1$ eV. Examples of clean reducing agents, which may be represented as hydrogen donors include hydrazine and hydroxylamine.

In an embodiment of the invention the hydrogen donors are propan-2-ol, butan-2-ol, triethylammonium formate and a mixture of triethlammonium formate and formic acid.

The temperature at which the transfer hydrogenation can be carried out is comprised between 0° C. and 100° C., more specifically in the range of between 20° C. and 80° C. Of course, a person skilled in the art is also able to select the temperature as a function of the melting and boiling point of the starting and final products.

Certain compounds of Formula III and their corresponding transition metal complexes are new. Accordingly these compounds and their metal complexes are further embodiments of the present invention. In particular, the present invention also includes a compound selected from the group consisting of a compound of Formulae III(c), III(d), III(e), III(f) and III(g):

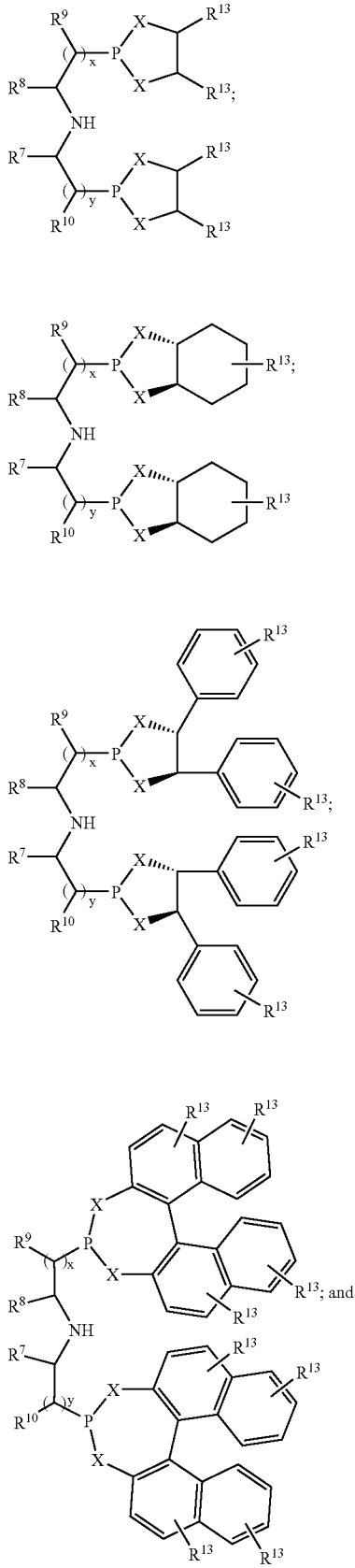

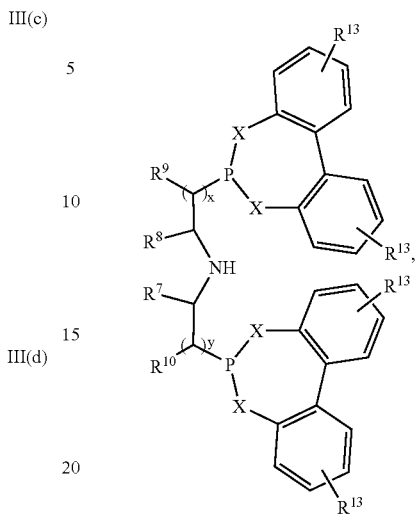

wherein
$R^7$ to $R^{10}$ simultaneously or independently are selected from the group consisting of H, $C_{1-20}$alkyl, $C_{2-20}$alkenyl, $C_{3-20}$cycloalkyl and aryl, said latter 4 groups being optionally substituted, or two adjacent or geminal groups are bonded together to form an optionally substituted ring;
$R^{13}$ simultaneously or independently are selected from the group consisting of H, halo, OH, $NH_2$, $OR^c$, $NR^c_2$ and $R^c$;
$R^c$ simultaneously or independently are selected from the group consisting of $C_{1-6}$alkyl, $C_{2-6}$alkenyl and aryl;
x and y simultaneously or independently are integers selected from the group consisting of 0, 1, 2, 3, and 4; and
X simultaneously or independently are $CH_2$, O, NH or $NR^c$.

In embodiments of the invention, the compound is a compound of formula III(c) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alky. In further embodiments of the invention $P_2NH$ is a compound of formula III(c) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

In embodiments of the invention, the compound is a compound of formula III(d) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl. In further embodiments of the invention $P_2NH$ is a compound of formula III(d) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

In embodiments of the invention, the compound is a compound of formula III(e) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl. In further embodiments of the invention $P_2NH$ is a compound of formula III(e) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

In embodiments of the invention, the compound is a compound of formula III(f) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl. In further embodiments of the invention $P_2NH$ is a compound of formula III(f) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

In embodiments of the invention, the compound is a compound of formula III(g) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl. In further embodiments of the invention $P_2NH$ is a compound of formula III(g) and $R^7$ to $R^{10}$ simultaneously or independently are selected from the group consisting of H, methyl and phenyl, specifically H, x and y simultaneously or independently are selected from the group consisting of 1 and 2, specifically 1, $R^{13}$ is $R^c$, in which $R^c$ is methyl and X is selected from the group consisting of $CH_2$, O and $NR^c$, in which $R^c$ is $C_{1-4}$alkyl, specifically methyl.

It is an embodiment of the invention that the compound is a compound of the formula III(f).

In specific embodiments of the invention, the compound is selected from the group consisting of:

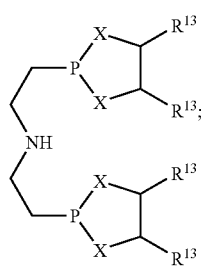

III(c)'

-continued

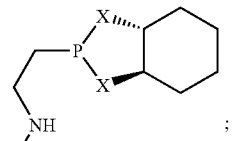

III(d)'

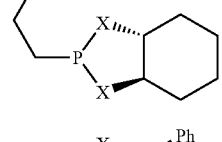

III(e)'

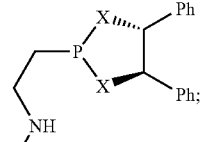

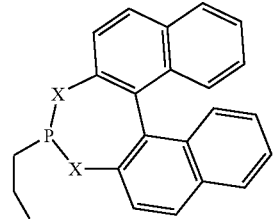

III(f)'

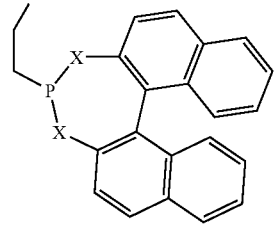

; and

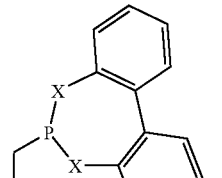

III(g)'

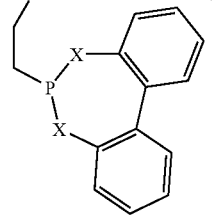

, wherein
$R^{13}$ simultaneously or independently are selected from the group consisting of H, halo, OH, $NH_2$, $OR^c$, $NR^c_2$ and $R^c$;
$R^c$ simultaneously or independently are selected from the group consisting of $C_{1-6}$alkyl, $C_{2-6}$alkenyl and aryl; and
X simultaneously or independently are $CH_2$, O, NH or $NR^c$.

In the compounds of formulae III(c)', III(d)', III(e)', III(f)' and III(g)', it is an embodiment of the invention that $R^{13}$ is H and both X groups in each compound are simultaneously $CH_2$, O or NMe.

In specific embodiments of the present invention, there is provided a compound selected from:

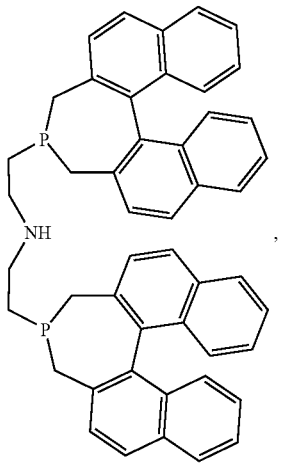

,

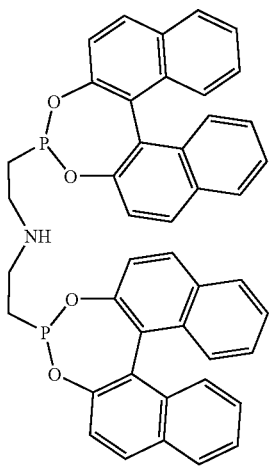

and

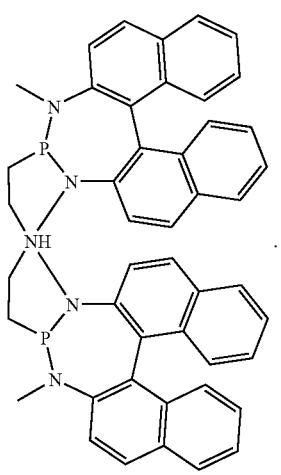

The present invention further includes the compound:

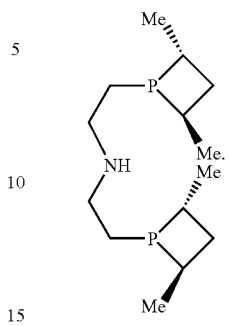

It is to be understood that the compounds of the invention include various acid addition salts where applicable.

The compounds of Formula III may be prepared using procedures known in the art. For example, these compounds may be prepared by reacting a compound of the Formula IV, wherein $R^7$-$R^{10}$ are as defined in Formula III with, for example, the lithium salts V (typically prepared in situ), wherein R is as defined in Formula II, under inert conditions at low temperatures, for example at about –78° C., as shown in Scheme 1.

Scheme 1

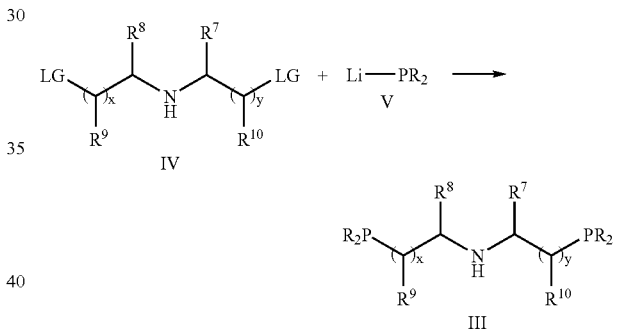

The present invention also includes transition metal complexes having the general formula II:

$$[M(P_2NH)Y_m] \quad \text{(II)}$$

wherein $P_2NH$ is selected from a compounds of the Formulae III(c)', III(d)', III(e)', III(f)' and III(g)', and M, Y and m are as defined above for Formula II. Procedures for the preparation of such complexes are described herein and are well known in the art.

The following non-limiting examples are illustrative of the present invention:

EXAMPLES

The invention will now be described in further details by way of the following examples, wherein the temperatures are indicated in degrees centigrade and the abbreviations have the usual meaning in the art. All the procedures described hereafter have been carried out under an inert atmosphere unless stated otherwise. All preparations and manipulations were carried out under $H_2$, $N_2$ or Ar atmospheres with the use of standard Schlenk, vacuum line and glove box techniques in dry, oxygen-free solvents. Tetrahydrofuran (THF), diethyl ether (Et$_2$O) and hexanes were dried and distilled from sodium benzophenone ketyl. Deuterated solvents were degassed and dried over activated molecular sieves. Ruthenium trichloride, iridium trichloride, chlorodiisopropylphosphine, chlorodiphenylphosphine, ketones and amines were purchased from Aldrich. The precursor compounds 2S,5S-2,5-hexanediol cyclic sulfate (Burk et al., *J. Am. Chem. Soc.,* 1993, 115, 10125), 2S,4S-2,4-pentanediol cyclic sulfate (Marinetti et al., *Chem. Eur. J.,* 1.999, 5, 1160), R,R-1 (Ini et al., *Organometallics,* 2001, 20, 3839), R,R-2 (Zhang et al., *Org. Lett.,* 1999, 1, 1679; *Tetrahedron Letters,* 2002, 43, 4849; Beller et al., *Angew. Chem. Int. Ed.,* 2001, 40, 3408) and R,R-3 (Shi et al., *Tetrahedron: Asymmetry,* 2002, 13, 2161; Denmark et al., *J. Am. Chem. Soc.,* 2001, 123, 6199) were prepared using the reported literature procedures. The diphosphine (H$_2$PC$_2$H$_4$)$_2$NSi(CH$_3$)$_3$ was prepared from tetraethyl-2,2'-iminobis(ethylphosphonate) (Varlet et al., *Phosphorus and sulfur* 1981, 10, 81; *Tetrahedron* 1981, 37, 1377) using established methods (Katti et al., *J. Org. Chem.* 2000, 65, 676; Hebler et al., *J. Organomet. Chem.* 1998, 553, 39). NMR spectra were recorded on a 300 MHz spectrometer (300 MHz for $^1$H, 75 MHz for $^{13}$C and 121.5 for $^{31}$P). All $^{31}$P chemical shifts were measured relative to 85% H$_3$PO$_4$ as an external reference. $^1$H and $^{13}$C chemical shifts were measured relative to partially deuterated solvent peaks but are reported relative to tetramethylsilane.

Example 1

Preparation of the Ligand Bis(2-(diisopropylphosphino)ethyl)amine, ($^i$Pr$_2$PC$_2$H$_4$)$_2$NH and Iridium Complexes

Example 1.1

Preparation of Bis(2-(diisopropylphosphino)ethyl)amine, ($^i$Pr$_2$PC$_2$H$_4$)$_2$NH

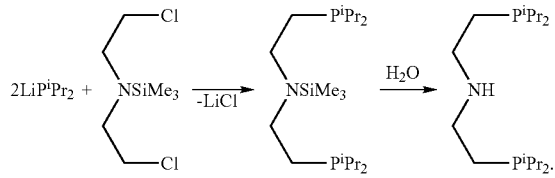

Chlorodiisopropylphosphine (11.0 g) was added in 2 g portions to a vigorously stirred suspension of lithium granules (1.5 g) in THF (30 ml) and the mixture was stirred for 3 days at room temperature. The mixture was filtered through a coarse sintered glass frit to remove excess lithium, then cooled to −80° C. and a solution of (ClC$_2$H$_4$)$_2$NSiMe$_3$ (7.75 g) in 10 ml of TFTF slowly added. The resulting suspension was allowed to slowly warm to room temperature and then refluxed for one hour. After cooling to room temperature, 15 ml of water was added and the mixture stirred for one hour. The aqueous layer was removed and another 15 ml of water and 15 ml of hexane added. The biphasic mixture was refluxed for 4 hours then cooled to room temperature. The aqueous layer was removed and the mixture evaporated to give the crude diphosphine. This was purified by distillation under vacuum. The fraction boiling at 120-140° C. was collected. Yield=9.72 g.

Example 1.2

Preparation of IrH$_2$Cl(($^i$Pr$_2$PC$_2$H$_4$)$_2$NH)

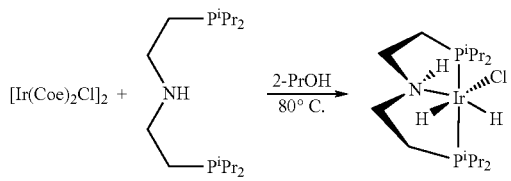

2-Propanol (3 ml) was added to a mixture of [Ir(coe)$_2$Cl]$_2$ (1.5 g) and ($^i$Pr$_2$PC$_2$H$_4$)$_2$NH (1.02 g) and the mixture warmed for 45 minutes at 60° C. Hexane (6 ml) was added to the cooled solution, and the resulting crystalline white solid was filtered, washed with hexanes and dried under vacuum. Yield=1.52 g. An X-ray crystal structure of this compound is shown in FIG. 1.

Example 1.3

Preparation of IrH$_3$(($^i$Pr$_2$PC$_2$H$_4$)$_2$NH)

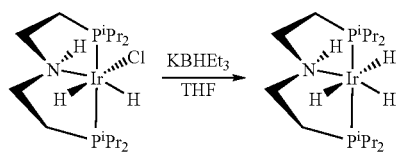

Method 1. A mixture of IrH$_2$Cl($^i$Pr$_2$PC$_2$H$_4$)$_2$NH (800 mg) in THF (2 ml) and lithium triethylborohydride (1600 mg of a 1.0 M solution in THF) was stirred for 12 hours at room temperature. The mixture was evaporated to dryness and extracted with 3×10 ml toluene and filtered. The combined filtrate was evaporated to dryness, yielding the trihydride product as a viscous, colourless oil, which solidified after 10 days at room temperature, yielding a white solid. Yield=628 mg.

Method 2. A mixture of IrH$_2$Cl(($^i$Pr$_2$PC$_2$H$_4$)$_2$NH) (800 mg) in THF (5 ml) and KO$^t$Bu (200 mg) was stirred for 10 minutes at room temperature. The mixture was filtered and 2-propanol (10 ml) added to the bright yellow solution, which immediately became colourless. The volume of the solvent was reduced to approximately 2 ml by evaporation under reduced pressure and hexane (10 ml) added. The crystalline white solid was filtered, washed with hexane and dried under vacuum. Yield=715 mg.

Example 1.4

Preparation of IrH$_2$((${}^i$Pr$_2$PC$_2$H$_4$)$_2$N)

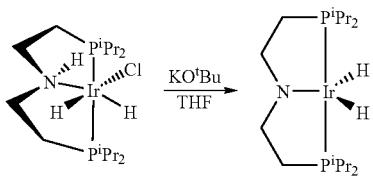

Tetrahydrofuran (2 ml) was added to a mixture of IrH$_2$Cl ((${}^i$Pr$_2$PC$_2$H$_4$)$_2$NH) (250 mg) and KO${}^t$Bu (75 mg) and the mixture stirred for 30 minutes at room temperature. The mixture was filtered to remove KCl and excess base and the filtrate evaporated to near dryness. Hexane (5 ml) was then added and the suspension stirred for 1 hour. The yellow crystalline product was filtered, washed with hexane and dried under vacuum. Yield=223 mg.

Example 2

Preparation of the Ligand Bis(((2R,4R)-2,4-dimethylphosphetane)ethyl)amine

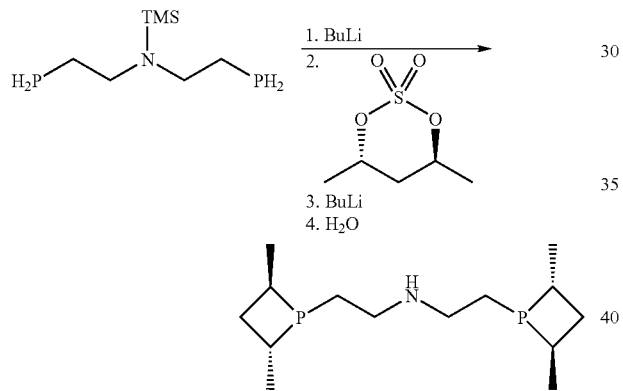

A solution of (H$_2$PC$_2$H$_4$)$_2$NSi(CH$_3$)$_3$ (200 mg, 0.96 mmol) in THF (10 ml) was cooled to −78° C. and BuLi (1.2 ml of a 1.6 M solution in hexane, 1.92 mmol) was added. The solution was allowed to warm to room temperature and stirred for 2 hours, then added to a solution of 2S,4S-2,4-pentanediol cyclic sulfate (320 mg, 1.92 mmol) in THF at −78° C. The reaction mixture was allowed to warm to room temperature and stirred for 1 hour. It was then cooled to −78° C. and BuLi (1.2 ml of a 1.6 M solution in hexane, 1.92 mmol) was added. The mixture was allowed to warm to room temperature and stirred for 6 hours. It was slowly hydrolyzed with 5 ml of water then stirred for one hour. The aqueous layer was removed and another 5 ml of water and 5 ml of hexane were added. The biphasic mixture was refluxed for 4 hours then cooled to room temperature. The aqueous layer was removed and the mixture was evaporated under vacuum to give the crude aminodiphospholane. This was purified by chromatography on alumina (hexane-ether) under nitrogen. Yield=163 mg, 62%. ${}^1$H NMR: δ 1.0 (dd, J$_{HH}$=7.2 Hz, J$_{HP}$=12.6 Hz, 6H, CH$_3$), 1.26 (dd, J$_{HH}$=7.3 Hz, J$_{HP}$=16.2 Hz, 6H, CH$_3$), 1.52 (s, br, 1H, NH), 1.60 (td, J$_{HH}$=7.7 Hz, J$_{HP}$=3.2 Hz, 4H, CH$_2$) 2.0-2.2 (m, 4H), 2.3-2.4 (m, 4H), 2.85 (m, 4H, CH$_2$). ${}^{31}$P{${}^1$H} NMR: δ 24.2 (s).

Example 3

Preparation of the Ligand Bis(((2R,5R)-2,5-dimethylphospholane)ethyl)amine and Iridium Complexes

Example 3.1

Preparation of Bis(((2R,5R)-2,5-dimethylphospholane)ethyl)amine

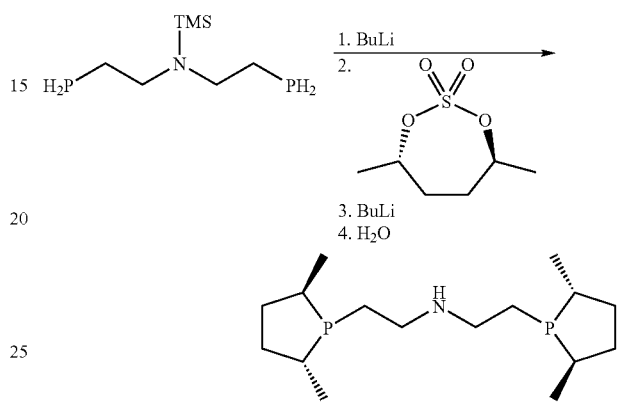

Bis(((2R,5R)-2,5-dimethylphospholane)ethyl)amine was prepared from 2S,5S-2,5-hexanediol cyclic sulfate (350 mg, 1.94 mmol) using a procedure similar to the one outlined in Example 2 for bis(((2R,4R)-2,4-dimethylphosphetane)ethyl)amine. Yield=208 mg, 71%. The NMR spectra are consistent with those reported in the literature (Burk et al., *Tetrahedron: Asymmetry*, 1991, 2, 569).

Example 3.2

Preparation of Chlorodihydrido[bis((2R,5R)-2,5-dimethylphospholanoethyl)amine]iridium(III)

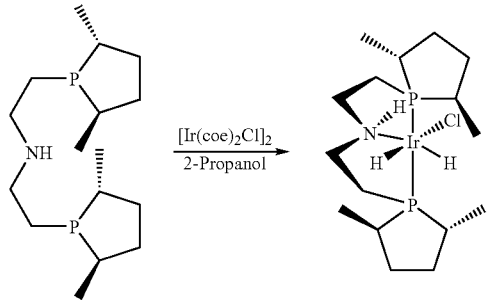

An aliquot of 2-propanol (2 ml) was added to a mixture of [Ir(coe)$_2$Cl]$_2$ (150 mg) and bis(((2R,5R)-2,5-dimethylphospholane)ethyl)amine (100 mg) and the mixture was warmed for 45 minutes at 60° C. under argon. It was cooled to room temperature and the volume was reduced to approximately 0.5 ml under reduced pressure. Hexane (5 ml) was added and the resulting crystalline white solid was filtered, washed with hexane and dried under vacuum. Yield=123 mg. ${}^1$H NMR: δ −24.2 (td, J$_{HH}$=7.9 Hz, J$_{HP}$=15.2 Hz, 1H, IrH), −19.3 (td, J$_{HH}$=8.0 Hz, J$_{HP}$=14.1 Hz, 1H, IrH), 0.94 (m, 6H, CH$_3$), 1.23 (m, 6H, CH$_3$), 1.32 (m, 4H), 1.41 (m, 6H), 1.52 (m, 2H), 1.71 (m, 4H), 2.82 (m, 4H, CH2), 3.72 (s, br, 1H, NH). ${}^{31}$P{${}^1$H} NMR: δ 46.2 (s).

Example 4

Preparation of the Aminodiphosphine Ligand III(f)-1

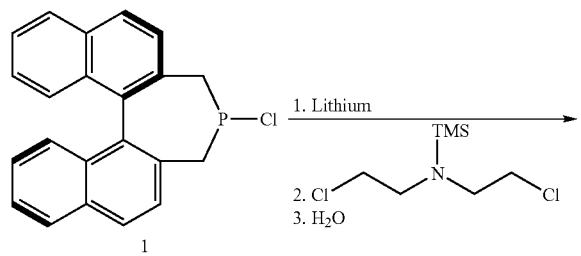

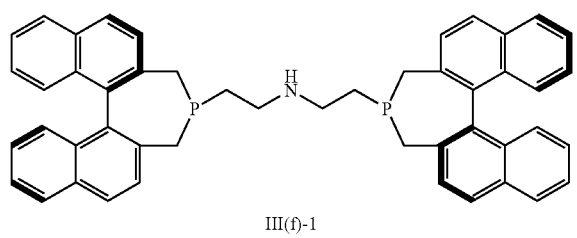

III(f)-1

Chlorophosphine R,R-1 (500 mg, 1.44 mmol) was added in portions to a vigorously stirred suspension of lithium granules (50 mg, 7.2 mmol) in THF (10 ml) and the mixture was stirred for 72 hours at room temperature. The mixture was filtered, cooled to −40° C. and a solution of $(ClC_2H_4)_2$ $NSiMe_3$ (150 mg, 0.70 mmol) in 10 ml of THF slowly added. The resulting suspension was allowed to slowly warm to room temperature and refluxed for one hour. After cooling to room temperature, 5 ml of water was added and the mixture was stirred for one hour. The aqueous layer was removed and another 5 ml of water and 10 ml of toluene were added. The biphasic mixture was refluxed for 4 hours and then cooled to room temperature. The aqueous layer was removed and the mixture was evaporated to give the aminodiphosphine product III(f)-1 as a tan-coloured solid. This was purified by chromatography on silica (toluene). Yield=355 mg, 73%. $^1H$ NMR: δ 1.71 (s, br, 1H, NH), 1.92 (m, 4H, $CH_2$), 2.2-2.6 (m, 8H, $CH_2$), 3.01 (m, 4H, $CH_2$), 6.93-7.81 (m, 24H, Ar). $^{31}P\{^1H\}$ NMR: δ 7.1 (s).

Example 5

Preparation of the Aminodiphosphine Ligand III(f)-2

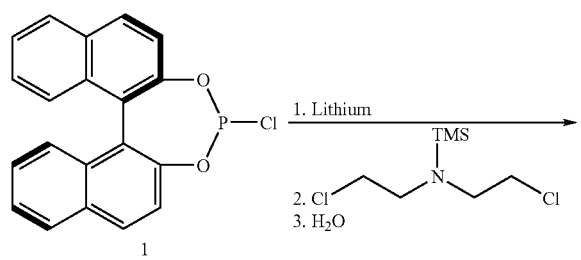

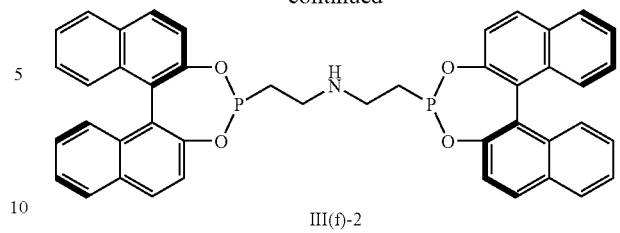

III(f)-2

This was prepared from chlorophosphine R,R-2 (500 mg) using a similar procedure for the preparation of III(f)-1. Yield=340 mg, 68%. $^1H$ NMR: δ 1.01 (s, br, 1H, NH), 1.84 (dd, $J_{HH}$=7.8 Hz, $J_{HP}$=4.2 Hz, 4H, $CH_2$), 2.92 (m, 4H, $CH_2$), 6.78-8.01 (m, 24H, Ar). $^{31}P\{^1H\}$ NMR: δ 196.3 (s).

Example 6

Preparation of the Aminodiphosphine Ligand II(f)-3

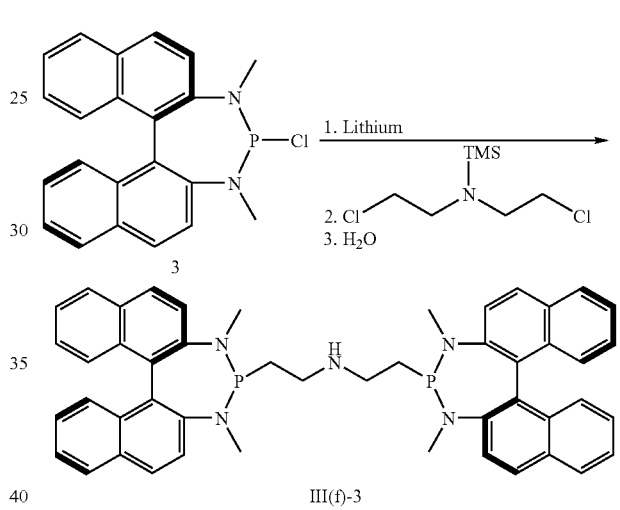

III(f)-3

This was prepared from chlorophosphine R,R-3 (500 mg) using a similar procedure for the preparation of III(f)-1, except that the reaction mixture was quenched by using 1.1 equivalent of water. Yield=380 mg, 76%. $^1H$ NMR: δ 1.92 (m, 4H, $CH_2$), 2.01 (s, br, 1H, NH), 2.81-3.02 (m, 12H, $CH_3$), 3.12 (m, 4H, $CH_2$), 6.70-8.02 (m, 24H, Ar). $^{31}P\{^1H\}$ NMR: δ 144.9 (s).

Example 7

Preparation of the Ligand Bis(2-(diphenylphosphino)ethyl)amine, $(Ph_2PC_2H_4)_2NH$ and Metal Complexes

Example 7.1

Preparation of $(Ph_2PC_2H_4)_2NH \cdot HCl$

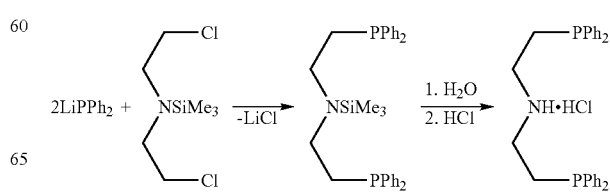

Chlorodiphenylphosphine (15.0 g) was added in 2 g portions to a vigorously stirred suspension of lithium granules (1.5 g) in THF (30 ml) and the mixture stirred for 3 days at room temperature. The mixture was cooled to −40° C. and a solution of (ClC$_2$H$_4$)$_2$NSiMe$_3$ (8.5 g) in 10 ml of THF was slowly added. The resulting suspension was then allowed to slowly warm to room temperature and refluxed for one hour. After cooling to room temperature, 15 ml of water was added and the mixture stirred for one hour. The aqueous layer was removed and another 15 ml of water and 15 ml of hexane added. The biphasic mixture was refluxed for 4 hours then cooled to room temperature. The aqueous layer was removed and the mixture evaporated to give the crude diphosphine. A 2M solution of aqueous HCl (200 ml) was added with vigorous stirring, resulting in the formation of the ammonium chloride salt of the diphosphine as a white solid. This was washed with water, cold methanol and hexanes, then dried under vacuum. Yield=14.32 g.

Example 7.2

Preparation of RuCl$_2$((Ph$_2$PC$_2$H$_4$)$_2$NH)

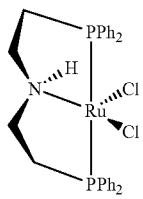

2-Propanol (3 ml) was added to a mixture of [RuCl$_2$(benzene)]$_2$ (250 mg), NEt$_3$ (200 mg) and (Ph$_2$PC$_2$H$_4$)$_2$NH.HCl (480 mg) and the mixture refluxed for 4 hours. The mixture was cooled to room temperature and the yellow solid filtered and washed with 2-propanol then dried under vacuum. Yield 372 mg.

Example 8

Transfer Hydrogenation of Acetophenone Using Iridium Catalysts Derived from Bis(2-(diisopropylphosphino)ethyl)amine, ($^i$Pr$_2$PC$_2$H$_4$)$_2$NH

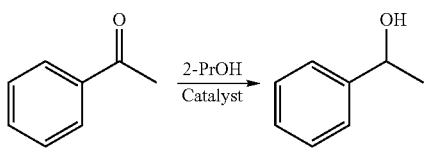

Example 8.1

Transfer Hydrogenation of Acetophenone Using IrH$_3$(($^i$Pr$_2$PC$_2$H$_4$)$_2$NH) as Catalyst A weighed amount of IrH$_3$(($^i$Pr$_2$PC$_2$H$_4$)$_2$NH) is added to a solution of acetophenone in 2-propanol (ketone:2-PrOH approx. 1:10) and the mixture stirred at the required temperature. The reaction progress is monitored using NMR. After attainment of an equilibrium conversion, the solvent is removed by evaporation under reduced pressure. A typical example is illustrated below:

IrH$_3$(($^i$Pr$_2$PC$_2$H$_4$)$_2$NH) (5 mg) is added to a solution of acetophenone (2.8 g) in 2-propanol (15 g) and the reaction mixture stirred for 1 hour at room temperature. The NMR of the reaction mixture showed 85% conversion of the ketone to the alcohol. The solvent was evaporated under reduced pressure, resulting in >99% phenyl ethanol. The results are presented in Table 1.

Example 8.2

Transfer Hydrogenation of Acetophenone Using IrH$_2$Cl(($^i$Pr$_2$PC$_2$H$_4$)$_2$NH)/KO$^t$Bu as Catalyst A weighed amount of IrH$_2$Cl(($^i$Pr$_2$PC$_2$H$_4$)$_2$NH) and KO$^t$Bu (catalyst:base aprox. 1:10) is added to a solution of acetophenone in 2-propanol (ketone:2-PrOH approx. 1:10) and the mixture stirred at the required temperature. The reaction progress is monitored using NMR. After attainment of an equilibrium conversion, the solvent is removed by evaporation under reduced pressure. A typical example is illustrated below:

IrH$_2$Cl(($^i$Pr$_2$PC$_2$H$_4$)$_2$NH) (5 mg) and KO$^t$Bu (10 mg) is added to a solution of acetophenone (2.8 g) in 2-propanol (15 g) and the reaction mixture stirred for 1 hour at room temperature. The NMR of the reaction mixture showed 84% conversion of the ketone to the alcohol. The solvent was evaporated under reduced pressure, resulting in >99% phenyl ethanol. The results are presented in Table 2.

Example 8.3

Transfer Hydrogenation of Acetophenone Using IrH$_2$(($^i$Pr$_2$PC$_2$H$_4$)$_2$N) as Catalyst A weighed amount of IrH$_2$(($^i$Pr$_2$PC$_2$H$_4$)$_2$N) is added to a solution of acetophenone in 2-propanol (ketone:2-PrOH approx. 1:10) and the mixture stirred at the required temperature. The reaction progress is monitored using NMR. After attainment of an equilibrium conversion, the solvent is removed by evaporation under reduced pressure. A typical example is illustrated below:

IrH$_2$(($^i$Pr$_2$PC$_2$H$_4$)$_2$N) (5 mg) is added to a solution of acetophenone (2.8 g) in 2-propanol (15 g) and the reaction mixture stirred for 1 hour at room temperature. The NMR of the reaction mixture showed 82% conversion of the ketone to the alcohol. The solvent was evaporated under reduced pressure, resulting in >99% phenyl ethanol. The results are presented in Table 3.

Example 9

Transfer Hydrogenation of Acetophenone Using Chlorodihydrido[bis((2R,5R)-2,5-dimethylphospholanoethyl)amine]iridium(III) as Catalyst

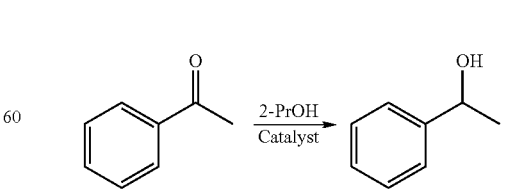

A weighed amount of the catalyst and KO$^t$Bu (10 mg) is added to a solution of acetophenone in 2-propanol and the mixture stirred at the required temperature for the desired time. The solvent is then removed by evaporation under reduced pressure. A typical example is illustrated below:

The catalyst (5 mg) is added to a solution of acetophenone (2.0 g) in 2-propanol (10 g) and the reaction mixture stirred for 2 hours at room temperature. The solvent was then evaporated under reduced pressure. The conversion was determined using NMR. The optical purity was determined by rotation. The results are presented in Table 4.

Example 10

Transfer Hydrogenation of Benzophenone Using Iridium Catalysts Derived from Bis(2-(diisopropylphosphino)ethyl)amine, $(^iPr_2PC_2H_4)_2NH$

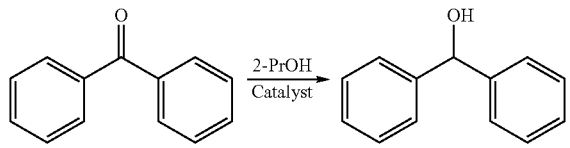

Example 10.1

Transfer Hydrogenation of Benzophenone Using $IrH_3((^iPr_2PC_2H_4)_2NH)$ as Catalyst A weighed amount of $IrH_3((^iPr_2PC_2H_4)_2NH)$ is added to a solution of benzophenone in 2-propanol and the mixture stirred at the required temperature. The reaction progress is monitored using NMR. After attainment of an equilibrium conversion, the solvent is removed by evaporation under reduced pressure. A typical example is illustrated below:

$IrH_3((^iPr_2PC_2H_4)_2NH)$ (5 mg) is added to a solution of benzophenone (2.0 g) in 2-propanol (10 g) and the reaction mixture stirred for 1 hour at room temperature. The NMR of the reaction mixture showed 92% conversion of the ketone to the alcohol. The solvent was evaporated under reduced pressure, resulting in >99% benzhydrol. The results are presented in Table 5.

Example 10.2

Transfer Hydrogenation of Benzophenone Using $IrH_2Cl((^iPr_2PC_2H_4)_2NH)/KO^tBu$ as Catalyst A weighed amount of $IrH_2Cl((^iPr_2PC_2H_4)_2NH)$ and $KO^tBu$ (catalyst:base aprox. 1:10) is added to a solution of benzophenone in 2-propanol (ketone:2-PrOH approx. 1:10) and the mixture stirred at the required temperature. The reaction progress is monitored using NMR. After attainment of an equilibrium conversion, the solvent is removed by evaporation under reduced pressure. A typical example is illustrated below:

$IrH_2Cl((^iPr_2PC_2H_4)_2NH)$ (5 mg) and $KO^tBu$ (10 mg) is added to a solution of benzophenone (2.0 g) in 2-propanol (10 g) and the reaction mixture stirred for 1 hour at room temperature. The NMR of the reaction mixture showed 91% conversion of the ketone to the alcohol. The solvent was evaporated under reduced pressure, resulting in >99% phenyl ethanol. The results are presented in Table 6.

Example 11

Transfer Hydrogenation of Benzylidene Acetone Using Iridium Catalysts Derived from Bis(2-(diisopropylphosphino)ethyl)amine, $(^iPr_2PC_2H_4)_2NH$

Example 11.1

Transfer Hydrogenation of Benzylidene Acetone Using $IrH_3((^iPr_2PC_2H_4)_2NH)$ as Catalyst A weighed amount of $IrH_3((^iPr_2PC_2H_4)_2NH)$ is added to a solution of benzylidene acetone in 2-propanol and the mixture stirred at the required temperature. The reaction progress is monitored using NMR. After attainment of an equilibrium conversion, the solvent is removed by evaporation under reduced pressure. A typical example is illustrated below:

$IrH_3((^iPr_2PC_2H_4)_2NH)$ (5 mg) is added to a solution of benzylidene acetone (2.0 g) in 2-propanol (10 g) and the reaction mixture stirred for 1 hour at room temperature. The solvent was evaporated under reduced pressure, resulting in >99% of the saturated alcohol. The results are presented in Table 7.

Example 11.2

Transfer Hydrogenation of Benzylidene Acetone Using $IrH_2Cl((^iPr_2PC_2H_4)_2NH)/KO^tBu$ as Catalyst A weighed amount of $IrH_2Cl((^iPr_2PC_2H_4)_2NH)$ and $KO^tBu$ (catalyst:base aprox. 1:10) is added to a solution of benzylidene acetone in 2-propanol (ketone:2-PrOH approx. 1:10) and the mixture stirred at the required temperature. The reaction progress is monitored using NMR. After attainment of an equilibrium conversion, the solvent is removed by evaporation under reduced pressure. A typical example is illustrated below:

$IrH_2Cl((^iPr_2PC_2H_4)_2NH)$ (5 mg) and $KO^tBu$ (10 mg) is added to a solution of benzylidene acetone (2.0 g) in 2-propanol (10 g) and the reaction mixture stirred for 1 hour at room temperature. The solvent was evaporated under reduced pressure, resulting in >99% of the saturated alcohol. The results are presented in Table 8.

Example 12

Transfer Hydrogenation of Cyclohexanone Using Iridium Catalysts Derived from Bis(2-(diisopropylphosphino)ethyl)amine, $(^iPr_2PC_2H_4)_2NH$

Example 12.1

Transfer Hydrogenation of Cyclohexanone Using IrH$_3$(($^i$Pr$_2$PC$_2$H$_4$)$_2$NH) as Catalyst A weighed amount of IrH$_3$(($^i$Pr$_2$PC$_2$H$_4$)$_2$NH) is added to a solution of cyclohexanone in 2-propanol and the mixture stirred at the required temperature. The reaction progress is monitored using NMR. After attainment of an equilibrium conversion, the solvent is removed by evaporation under reduced pressure. A typical example is illustrated below:

IrH$_3$(($^i$Pr$_2$PC$_2$H$_4$)$_2$NH) (5 mg) is added to a solution of cyclohexanone (2.0 g) in 2-propanol (10 g) and the reaction mixture stirred for 1 hour at room temperature. The solvent was evaporated under reduced pressure, resulting in >99% of the saturated alcohol. The results are presented in Table 9.

Example 12.2

Transfer Hydrogenation of Cyclohexanone Using IrH$_2$Cl(($^i$Pr$_2$PC$_2$H$_4$)$_2$NH)/KO$^t$Bu as Catalyst A weighed amount of IrH$_2$Cl(($^i$Pr$_2$PC$_2$H$_4$)$_2$NH) and KO$^t$BU (catalyst:base aprox. 1:10) is added to a solution of cyclohexanone in 2-propanol (ketone:2-PrOH approx. 1:10) and the mixture stirred at the required temperature. The reaction progress is monitored using NMR. After attainment of an equilibrium conversion, the solvent is removed by evaporation under reduced pressure. A typical example is illustrated below:

IrH$_2$Cl(($^i$Pr$_2$PC$_2$H$_4$)$_2$NH) (5 mg) and KO$^t$Bu (10 mg) is added to a solution of cyclohexanone (2.0 g) in 2-propanol (10 g) and the reaction mixture stirred for 1 hour at room temperature. The solvent was evaporated under reduced pressure, resulting in >99% of the saturated alcohol. The results are presented in Table 10.

Example 13

Transfer Hydrogenation N-(Benzylidene)phenylamine Using Iridium Catalysts Derived from Bis(2-(diisopropylphosphino)ethyl)amine, ($^i$Pr$_2$PC$_2$H$_4$)$_2$NH

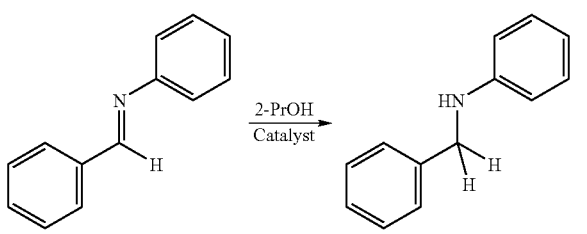

A weighed amount of the catalyst is added to a solution of N-(Benzylidene)phenylamine in 2-propanol and the mixture stirred at the required temperature. The reaction progress is monitored using NMR. After attainment of an equilibrium conversion, the solvent is removed by evaporation under reduced pressure. A typical example is illustrated below:

IrH$_3$(($^i$Pr$_2$PC$_2$H$_4$)$_2$NH) (5 mg) is added to a solution of N-(Benzylidene)phenylamine (1.5 g) in 2-propanol (10 g) and the reaction mixture stirred for 1 hour at 80° C. The solvent was evaporated under reduced pressure, to give the amine (93% yield). The results are presented in Table 11.

Example 14

Hydrogenation of Acetophenone Using Hydrogen Gas and Iridium Catalysts Derived from Bis(2-(diisopropylphosphino)ethyl)amine, ($^i$Pr$_2$PC$_2$H$_4$)$_2$NH

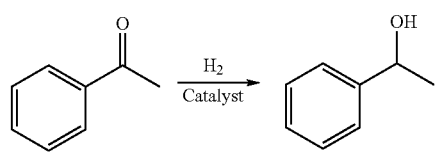

A weighed amount of the catalyst is added to a solution of acetophenone in benzene and the mixture stirred under hydrogen gas (3 atm) at the required temperature. The reaction progress was monitored using NMR. The results are presented in Table 12.

Example 15

Transfer Hydrogenation of Ketones Using an Iridium Catalyst Generated In Situ from (Ph$_2$PC$_2$H$_4$)$_2$NH.HCl (5 mg), [Ir(coe)$_2$Cl]$_2$ (5 mg) and KO$^t$Bu (10 mg)

Weighed amounts of [Ir(coe)$_2$Cl]$_2$, (Ph$_2$PC$_2$H$_4$)$_2$NH.HCl and KO$^t$Bu are mixed together in an aliquot of 2-propanol. The required amount of the substrate and 2-propanol are then added and the mixture stirred at the required temperature for the desired time. The reaction progress is monitored using NMR.

The transfer hydrogenation of acetophenone is illustrated below:

2-Propanol (1 ml) is added to a mixture of (Ph$_2$PC$_2$H$_4$)$_2$NH.HCl (5 mg), [Ir(coe)$_2$Cl]$_2$ (5 mg) and KO$^t$Bu (10 mg) at room temperature in a 50 ml round bottom flask and the solution stirred for 10 minutes. Acetophenone (3.0 g) and 2-propanol (12 g) are then added and the reaction mixture stirred for 1 hour at 60° C. The results are presented in Table 13.

Example 16

Transfer Hydrogenation of Acetophenone Using an Iridium Catalyst Generated In Situ from an Aminodiphosphine Ligand, [Ir(coe)$_2$Cl]$_2$ and KO$^t$Bu Weighed amounts of [Ir(coe)$_2$Cl]$_2$, the aminodiphosphine ligand and KO$^t$Bu are mixed together in an aliquot of 2-propanol. Acetophenone and 2-propanol are then added and the mixture stirred at the required temperature for the desired time. The transfer hydrogenation of acetophenone is illustrated below:

2-Propanol (1 ml) is added to a mixture of bis(((2R,5R)-2,5-dimethylphospholane)-ethyl)amine (5 mg), [Ir(coe)$_2$Cl]$_2$ (8 mg) and KO$^t$Bu (10 mg) at room temperature in a round bottom flask and the solution stirred for 10 minutes. Acetophenone (2.0 g) and 2-propanol (10 g) are then added and the reaction mixture stirred for 2 hours at room temperature. The solvent was removed under reduced pressure and the product analyzed by NMR. The e.e. was assayed by rotation. The results are presented in Table 14.

Example 17

Transfer Hydrogenation of Acetophenone Using HCOOH/NEt₃ and an Iridium Catalyst Generated In Situ from (Ph₂PC₂H₄)₂NH.HCl, [Ir(coe)₂]₂ and KO'Bu

Triethylammonium formate (1.0 g HCOOH/NEt₃, 5:2) is added to a mixture of (Ph₂PC₂H₄)₂NH.HCl (5 mg), [Ir(coe)₂Cl]₂ (5 mg), KO'Bu (10 mg) and acetophenone (1.0 g) and the resulting solution stirred for 8 hours at 60° C. the NMR spectrum of the reaction mixture showed 75% conversion of the ketone to phenyl ethanol.

Example 18

Transfer Hydrogenation of Acetophenone Using a Rhodium Catalyst Generated In Situ from (ⁱPr₂PC₂H₄)₂NH, [Rh(cod)Cl]₂ and KO'Bu 2-Propanol (1 ml) is added to a mixture of (ⁱPr₂PC₂H₄)₂NH (15 mg), [Rh(cod)Cl]₂ (10 mg) and KO'Bu (10 mg) at room temperature in a 50 ml round bottom flask and the solution stirred for 10 minutes. Acetophenone (1.5 g) and 2-propanol (7.5 g) are then added and the reaction mixture stirred for 1 hour at 80° C. The NMR of the reaction mixture showed 82% conversion of the ketone to phenyl ethanol.

Example 19

Transfer Hydrogenation of Acetophenone Using a Ruthenium Catalyst

2-Propanol (10 ml) is added to a mixture of RuCl₂[(Ph₂PC₂H₄)₂NH] (10 mg), acetophenone (2.0 g) and KO'Bu (10 mg) and the reaction mixture stirred for 1 hour at 80° C. The NMR of the reaction mixture showed 79% conversion of the ketone to phenyl ethanol.

Example 20

Catalytic Hydrogenation of Ketones and Imines with Ruthenium Catalysts

In a typical catalytic hydrogenation procedure, weighed amounts of the catalyst and KO'Bu are added to a solution of the neat substrate or its solution in 2-propanol and the mixture is then stirred at the required temperature under 3 atm of H₂ gas. The reaction progress is monitored using NMR.

The hydrogenation of acetophenone is illustrated below:

The catalyst (10 mg) and KO'Bu (10 mg) is added to a solution of neat acetophenone (1.0 g) and the reaction mixture stirred for 3 hours at room temperature. The proton NMR spectrum of the reaction mixture showed 100% conversion of the ketone to the alcohol. The results are shown in Table 15.

Example 21

Hydrogenation Reactions Using an In Situ Generated Ruthenium

In a typical catalytic hydrogenation procedure using an in situ generated ruthenium catalyst, weighed amounts of [RuCl₂(benzene)]₂, the ligand and KO'Bu are mixed together in an aliquot of toluene. The required amount of the substrate and 2-propanol are then added and the mixture stirred at the required temperature for the desired time under an atmosphere of hydrogen gas. The hydrogenation of acetophenone is illustrated below:

A weighed amount of (Ph₂PC₂H₄)₂NH (10 mg), [RuCl₂(benzene)]₂ (10 mg) and KO'Bu (10 mg) in toluene (1 ml) are mixed together at room temperature in a round bottom flask. Acetophenone (2.0 g) and 2-propanol (2 g) are then added and the reaction mixture stirred for 1 hour at room temperature under hydrogen gas (3 atm). The NMR spectrum shows complete conversion of the ketone after 3 hours.

The results are shown in Table 16.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Performance of IrH₃((ⁱPr₂PC₂H₄)₂NH) as catalyst for the transfer hydrogenation of acetophenone.

| Run | Temp/° C. | Mass Substrate | Mass Catalyst | S:C Ratio | Time | Yield/% |
|---|---|---|---|---|---|---|
| 1 | 25 | 2.8 g | 5 mg | 2,300 | 1 hr | >99 |
| 2 | 25 | 5.6 g | 5 mg | 4,600 | 2 hr | >99 |
| 3 | 60 | 11.2 g | 5 mg | 9,200 | 1 hr | 96 |
| 4 | 60 | 22.5 g | 5 mg | 19,000 | 2 hr | 97 |
| 5 | 60 | 45 g | 5 mg | 38,000 | 5 hr | 94 |

TABLE 2

Performance of IrH₂Cl((ⁱPr₂PC₂H₄)₂NH)/KO'Bu as catalyst for the transfer hydrogenation of acetophenone.

| Run | Temp/° C. | Mass Substrate | Mass Catalyst | S:C Ratio | Time | Yield/% |
|---|---|---|---|---|---|---|
| 1 | 25 | 2.8 g | 5 mg | 2,300 | 1 hr | >99 |
| 2 | 25 | 5.6 g | 5 mg | 4,600 | 2 hr | >99 |
| 3 | 60 | 11.2 g | 5 mg | 9,200 | 1 hr | 98 |

TABLE 3

Performance of $IrH_2((^iPr_2PC_2H_4)_2N)$ as catalyst for the transfer hydrogenation of acetophenone.

| Run | Temp/°C. | Mass Substrate | Mass Catalyst | S:C Ratio | Time | Yield/% |
|---|---|---|---|---|---|---|
| 1 | 25 | 2.8 g | 5 mg | 2,300 | 1 hr | >99 |
| 2 | 25 | 5.6 g | 5 mg | 4,600 | 2 hr | >99 |

TABLE 4

Performance of Chlorodihydrido[bis((2R,5R)-2,5-dimethylphospholanoethyl)amine]-iridium(III) as catalyst for the transfer hydrogenation of acetophenone.

| Run | Temp/°C. | Mass Substrate | Mass Catalyst | S:C Ratio | Time | Yield/% | e.e./% |
|---|---|---|---|---|---|---|---|
| 1 | 30 | 2.0 g | 5 mg | 1800 | 2 hr | >99 | 69 (R) |
| 2 | 60 | 5.0 g | 5 mg | 4500 | 4 hr | >99 | 56 (R) |

TABLE 5

Performance of $IrH_3((^iPr_2PC_2H_4)_2NH)$ as catalyst for the transfer hydrogenation of benzophenone.

| Run | Temp/°C. | Mass Substrate | Mass Catalyst | S:C Ratio | Time | Yield/% |
|---|---|---|---|---|---|---|
| 1 | 25 | 2.0 g | 5 mg | 1,100 | 10 min | >99 |
| 2 | 25 | 16.5 g | 5 mg | 9,100 | 2.5 hr | >99 |
| 3 | 25 | 30.0 g | 3 mg | 27,500 | overnight | >99 |

TABLE 6

Performance of $IrH_2Cl((^iPr_2PC_2H_4)_2NH)/KO^tBu$ as catalyst for the transfer hydrogenation of benzophenone.

| Run | Temp/°C. | Mass Substrate | Mass Catalyst | S:C Ratio | Time | Yield/% |
|---|---|---|---|---|---|---|
| 1 | 25 | 2.0 g | 5 mg | 1,100 | 1 hr | >99 |
| 2 | 25 | 16.5 g | 5 mg | 9,100 | 2.5 hr | >99 |

TABLE 7

Performance of $IrH_3((^iPr_2PC_2H_4)_2NH)$ as catalyst for the transfer hydrogenation of benzylidene acetone.

| Run | Temp/°C. | Mass Substrate | Mass Catalyst | S:C Ratio | Time | Yield/% |
|---|---|---|---|---|---|---|
| 1 | 25 | 2.0 g | 5 mg | 1,400 | 1 hr | >99 |
| 2 | 25 | 5.0 g | 5 mg | 3,400 | 2 hr | >99 |

TABLE 8

Performance of $IrH_2Cl((^iPr_2PC_2H_4)_2NH)/KO^tBu$ as catalyst for the transfer hydrogenation of benzylidene acetone.

| Run | Temp/°C. | Mass Substrate | Mass Catalyst | S:C Ratio | Time | Yield/% |
|---|---|---|---|---|---|---|
| 1 | 25 | 2.0 g | 5 mg | 1,400 | 1 hr | >99 |
| 2 | 25 | 5.0 g | 5 mg | 3,400 | 2 hr | >99 |

TABLE 9

Performance of $IrH_3((^iPr_2PC_2H_4)_2NH)$ as catalyst for the transfer hydrogenation of cyclohexanone.

| Run | Temp/°C. | Mass Substrate | Mass Catalyst | S:C Ratio | Time | Yield/% |
|---|---|---|---|---|---|---|
| 1 | 25 | 2.0 g | 5 mg | 2,000 | 10 min | >99 |
| 2 | 25 | 5.0 g | 5 mg | 5,000 | 1 hr | >99 |

TABLE 10

Performance of $IrH_2Cl((^iPr_2PC_2H_4)_2NH)/KO^tBu$ as catalyst for the transfer hydrogenation of cyclohexanone.

| Run | Temp/°C. | Mass Substrate | Mass Catalyst | S:C Ratio | Time | Yield/% |
|---|---|---|---|---|---|---|
| 1 | 25 | 2.0 g | 5 mg | 2,000 | 1 hr | >99 |
| 2 | 25 | 5.0 g | 5 mg | 5,000 | 1 hr | >99 |

TABLE 11

Performance of Iridium complexes as catalyst for the transfer hydrogenation of N-(Benzylidene)phenylamine.

| Catalyst | Temp/°C. | Mass Substrate | Mass Catalyst | S:C Ratio | Time | Yield/% |
|---|---|---|---|---|---|---|
| $IrH_3((^iPr_2PC_2H_4)_2NH)$ | 80 | 1.5 g | 5 mg | 800 | 1 hr | 93 |
| $IrH_2Cl((^iPr_2PC_2H_4)_2NH)/KO^tBu$ | 80 | 1.0 g | 5 mg | 550 | 1 hr | 96 |
| $IrH_2((^iPr_2PC_2H_4)_2N)$ | 80 | 1.0 g | 5 mg | 550 | 1 hr | 94 |

TABLE 12

Performance of Iridium catalysts for the hydrogenation of acetophenone.

| Catalyst | Temp/°C. | Mass Substrate | Mass Catalyst | S:C Ratio | Time | Yield/% |
|---|---|---|---|---|---|---|
| $IrH_3((^iPr_2PC_2H_4)_2NH)$ | 25 | 1.0 g | 5 mg | 800 | 12 hr | 0 |
| $IrH_2Cl((^iPr_2PC_2H_4)_2NH)/KO^tBu$ | 25 | 1.0 g | 5 mg | 800 | 12 hr | <1 |
| $IrH_2((^iPr_2PC_2H_4)_2N)$ | 25 | 1.0 g | 5 mg | 800 | 12 hr | 0 |

TABLE 13

Performance of in situ generated iridium catalyst for the transfer hydrogenation of ketones using (Ph$_2$PC$_2$H$_4$)$_2$NH.HCl (5 mg), [Ir(coe)$_2$Cl]$_2$ (5 mg) and KO$^t$Bu (10 mg).

| Substrate | Temp/° C. | Mass Substrate | Mass 2-PrOH | Time | Conv. % |
|---|---|---|---|---|---|
| acetophenone | 60 | 1.0 g | 5 g | 20 min | 81 |
| acetophenone | 60 | 3.0 g | 12 g | 1 hour | 82 |
| benzophenone | 60 | 1.0 g | 5 g | 20 min | 94 |
| benzophenone | 60 | 3.0 g | 12 g | 1 hour | 93 |

TABLE 14

Performance of in situ generated iridium catalyst for the transfer hydrogenation of acetophenone.

| Ligand | Temp/° C. | S:C | Time | Conv. % |
|---|---|---|---|---|
| (phospholane ligand) | 30 | 1000 | 2 hr | >99 |
| (phosphetane ligand) | 30 | 1000 | 2 hr | >99 |
| (binaphthyl ligand) | 60 | 500 | 2 hr | 88 |

TABLE 14-continued

Performance of in situ generated iridium catalyst for the transfer hydrogenation of acetophenone.

| Ligand | Temp/° C. | S:C | Time | Conv. % |
|---|---|---|---|---|
| [structure: binaphthyl phosphite-NH-phosphite binaphthyl ligand] | 60 | 500 | 2 hr | 93 |
| [structure: binaphthyl diamino phosphine-NH-phosphine binaphthyl diamino ligand] | 60 | 500 | 2 hr | 12 |

TABLE 15

Performance of $RuCl_2(PPh_2PC_2H_4)_2NH$ as catalyst for the hydrogenation of various ketones and imines

| Substrate | Temp/° C. | Mass Substrate | Mass Catalyst | Time | Isolated Yield/% |
|---|---|---|---|---|---|
| [acetophenone] | 25 | 1.0 g | 10 mg | 3 hr | 100 |
| [benzophenone] | 25 | 2.0 g | 10 mg | 3 hr | 100 |
| [cyclohexanone] | 25 | 2.0 g | 10 mg | 3 hr | 100 |
| [N-benzylideneaniline] | 25 | 1.5 g | 10 mg | 1 hr | 100 |

TABLE 16

Performance of in situ generated ruthenium catalyst for the hydrogenation of ketones using $(Ph_2PC_2H_4)_2NH \cdot HCl$ (10 mg), $[RuCl_2(benzene)]_2$ (10 mg) and $KO^tBu$ (5 mg).

| Substrate | Temp/° C. | Mass Substrate | Mass 2-PrOH | Time | Conv. % |
|---|---|---|---|---|---|
|  | 25 | 2.0 g | 2 g | 3 hr | 100 |
| 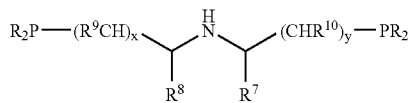 | 25 | 2.0 g | 2 g | 3 hr | 100 |
| 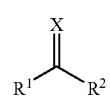 | 25 | 1.0 g | 2 g | 3 hr | 100 |

What is claimed is:

1. A process for the reduction of compounds comprising a carbon-oxygen (C=O) double bond, to a corresponding hydrogenated alcohol comprising contacting a compound comprising the C=O double bond with a hydrogen donor and a catalyst comprising a metal complex having a tridentate aminodiphosphine ligand under transfer hydrogenation conditions, wherein the catalyst comprises a metal complex with a tridentate aminodiphosphine ligand of the formula (II)

$$[M(P_2NH)Y_m] \qquad (II)$$

wherein

M is a metal;

Y simultaneously or independently are any anionic or neutral ligand;

m is an integer representing the number of ligands Y that are required to fulfill the valency requirements of M; and the ligand ($P_2NH$) represents a tridentate aminodiphosphine ligand of formula (III):

$$R_2P-(R^9CH)_x\underset{R^8}{\overset{H}{\underset{|}{N}}}(CHR^{10})_y-PR_2 \qquad (III)$$

in which $R^7$ to $R^{10}$ simultaneously or independently are selected from the group consisting of H, $C_{1-20}$alkyl, $C_{2-20}$alkenyl, $C_{3-20}$cycloalkyl and aryl, said latter 4 groups being optionally substituted, or two adjacent or geminal groups are bonded together to form an optionally substituted ring;

x and y are, simultaneously or independently, equal to 0, 1, 2, 3 or 4; and

R is simultaneously or independently selected from the group consisting of H, $C_{1-20}$alkyl, aryl and $C_{2-20}$alkenyl, OR and $NR_2$, said latter 5 groups being optionally substituted, or the R groups on the same P atom may be linked together to form an optionally substituted monocyclic or polycyclic ring system having 4 or more atoms, including the phosphorous atom to which said R groups are bonded, which is saturated, unsaturated and/or aromatic and in which one or more carbon atoms in said monocyclic or polycyclic ring system may optionally be replaced with a heteroatom selected from O, S, N, and Si, wherein the optional substituents are selected from one or more of halo, OH, $NH_2$, $OR^c$, $NR^c_2$ and $R^c$, in which $R^c$ is selected from the group consisting of $C_{1-6}$alkyl, $C_{2-6}$alkenyl and aryl, and wherein the catalyst further optionally comprises a base.

2. The process according to claim 1, wherein the compound comprising a carbon-oxygen (C=O) double bond is a compound of formula (I):

$$\underset{R^1}{\overset{X}{\underset{\|}{\phantom{x}}}}\!\!R^2 \qquad (I)$$

wherein,

X is O; and $R^1$ and $R^2$ each simultaneously or independently are selected from the group consisting of H, aryl, $C_{1-20}$alkyl, $C_{2-20}$alkenyl, $C_{3-20}$cycloalkyl and heteroaryl, said latter 5 groups being optionally substituted, or $R^1$ and $R^2$ are linked to form an optionally substituted ring;

wherein heteroaryl is a mono- or bicyclic heteroaromatic radical containing from 5 to 10 atoms, of which 1-3 atoms may be a heteroatom selected from the group consisting of S, O and N, and wherein the optional substituents are selected from the group consisting of halo, OH, $NH_2$, $OR^c$, $NR^c_2$ or $R^c$ groups, in which $R^c$ is selected from the group consisting of $C_{1-6}$alkyl, $C_{2-6}$alkenyl and aryl and one or more of the carbon atoms in the alkyl, alkenyl and cycloalkyl groups may be optionally replaced with a heteroatom selected from the group consisting of O, S, N, P or Si.

3. The process according to claim 2, wherein $R^1$ and $R^2$ are different.

4. The process according to claim 1, wherein in the tridentate ligand of formula III, $R^7$ to $R^{10}$ simultaneously or independently are selected from the group consisting of H, $C_{1-10}$alkyl, $C_{2-10}$alkenyl, $C_{3-10}$cycloalkyl and aryl, said latter 4 groups being optionally substituted, or two adjacent or geminal groups are bonded together to form an optionally substituted ring.

5. The process according to claim 4, wherein $R^7$ to $R^{10}$ simultaneously or independently are selected from the group consisting of H, $C_{1-4}$alkyl, $C_{2-4}$alkenyl, $C_{3-6}$cycloalkyl and aryl, said latter 4 groups being optionally substituted, or two adjacent or geminal groups are bonded together to form an optionally substituted ring, said ring containing 6 atoms, including the carbons to which said groups are attached.

6. The process according to claim 5, wherein $R^7$ to $R^{10}$ are all H.

7. The process according to claim 1, wherein in the tridentate ligand of formula III, x and y are simultaneously equal to 0, 1, 2, 3 or 4.

8. The process according to claim 7, wherein x and y are simultaneously equal to 0, 1 or 2.

9. The process according to claim 8, wherein x and y are simultaneously equal to 1.

10. The process according to claim 1, wherein in the tridentate ligand of formula III, R is simultaneously or independently selected from the group consisting of H, $C_{1-10}$alkyl, aryl and $C_{2-10}$alkenyl, said latter 3 groups being optionally substituted, or the R groups on the same P atom may be linked together to form an optionally substituted monocyclic or polycyclic ring system having 4 or more atoms, including the phosphorous atom to which said R groups are bonded, which is saturated, unsaturated and/or aromatic and in which one or more carbon atoms in said monocyclic or polycyclic ring system may optionally be replaced with a heteroatom selected from O and NH.

11. The process according to claim 10, wherein R is simultaneously or independently selected from the group consisting of H, $C_{1-6}$alkyl, phenyl, naphthyl and $C_{2-6}$alkenyl, said latter 3 groups being optionally substituted, or the R groups on the same P atom may be linked together to form an optionally substituted monocyclic, fused bicyclic, fused tricyclic, fused quadracyclic or fused pentacyclic ring system having 4-23 atoms, including the phosphorous atom to which said R groups are bonded, which is saturated, unsaturated and/or aromatic and in which one or more carbon atoms in said monocyclic or polycyclic ring system may optionally be replaced with a heteroatom selected from O and NH.

12. The process according to claim 11, wherein R is simultaneously $C_{1-6}$alkyl or phenyl.

13. The process according to claim 1, wherein the two R groups on each phosphorus atom are linked to form a monocyclic saturated ring containing from 4 to 7 atoms, including the phosphorus atom to which the R groups are attached, said ring being optionally substituted with 1 to 2 substituents independently selected from $C_{1-6}$alkyl, $C_{2-6}$alkenyl and aryl, and wherein one or two of the carbon atoms in the ring may be replaced with a heteroatom selected from O, S and N—$C_{1-4}$alkyl.

14. The process according to claim 13, wherein the monocyclic saturated ring contains 4-5 atoms, including the phosphorus atom to which the R groups are attached.

15. The process according to claim 13, wherein the substituents are independently selected from $C_{1-4}$alkyl, $C_{2-4}$alkenyl and phenyl.

16. The process according to claim 15, wherein the substituents are independently selected from methyl and phenyl.

17. The process according to claim 13, wherein the optional heteroatoms or optional substituents are located at positions alpha to the phosphorus atom.

18. The process according to claim 1, wherein the two R groups on the phosphorus atom are linked to form a polycyclic ring system comprising 3, 5 or 7 rings each ring may be fully saturated, partially unsaturated and/or aromatic and which are optionally substituted with 1 to 2 substituents independently selected from $C_{1-6}$alkyl, $C_{2-6}$alkenyl and aryl, and wherein one or two of the carbon atoms in the ring may be replaced with a heteroatom selected from O, S and N—$C_{1-4}$alkyl.

19. The process according to claim 18, wherein the optional substituents are independently selected from $C_{1-4}$alkyl, $C_{2-4}$alkenyl and phenyl.

20. The process according to claim 19, wherein the optional substituents are independently selected from methyl or phenyl.

21. The process according to claim 18, wherein one or two of the carbon atoms in the ring may be replaced with a heteroatom selected from O and N—$CH_3$.

22. The process according to claim 18, wherein any optional heteroatoms or optional substituents are located at positions alpha to the phosphorus atom.

23. The process according to claim 1, wherein both phosphorus atoms in the compounds of Formula II are identically substituted.

24. The process according to claim 1, wherein the optional substituents on the compounds of formula III are selected from one or more of halo, OH, $NH_2$, $CR^c$, $NR^c_2$ and $R^c$, in which $R^c$ is selected from the group consisting of $C_{1-4}$alkyl, $C_{2-4}$alkenyl and phenyl.

25. The process according to claim 1, wherein the groups $R^7$ to $R^{10}$ and R in the ligands of Formula III are unsubstituted.

26. The process according to claim 1, wherein the aminodiphosphine ligand ($P_2NH$) of formula (III) is chiral.

27. The process according to claim 1, wherein the ligand ($P_2NH$) is selected from formulae III(a)-III(g):

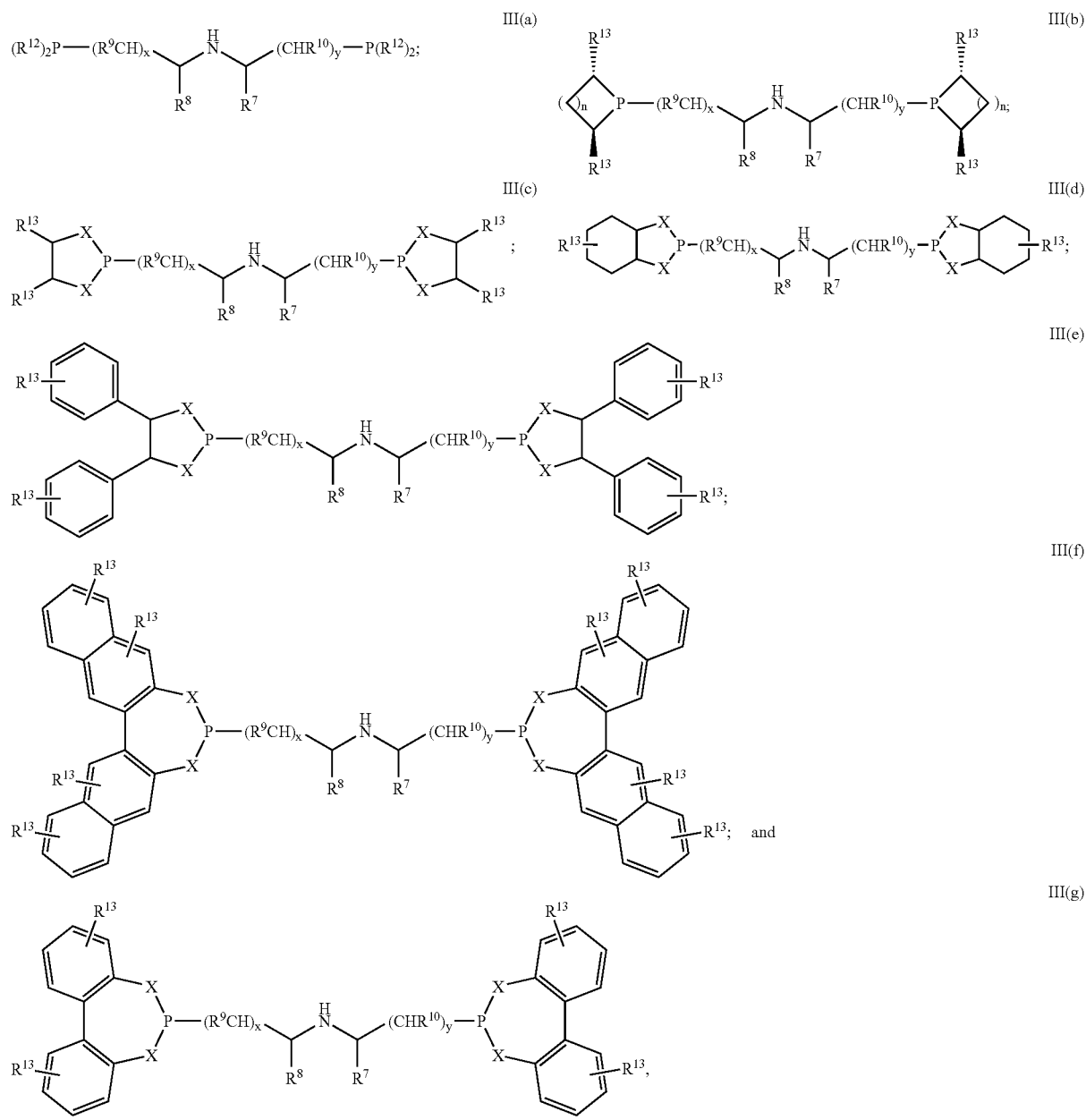

wherein
- $R^7$ to $R^{10}$ simultaneously or independently are selected from the group consisting of H, $C_{1-20}$alkyl, $C_{2-20}$alkenyl, $C_{3-20}$cycloalkyl and aryl, said latter 4 groups being optionally substituted, or two adjacent or geminal groups are bonded together to form an optionally substituted ring;
- $R^{12}$ simultaneously or independently are selected from the group consisting of halo, OH, $NH_2$, $OR^c$, $NR^c_2$ and $R^c$;
- $R^{13}$ simultaneously or independently are selected from the group consisting of H, halo, OH, $NH_2$, $OR^c$, $NR^c_2$ and $R^c$;
- $R^c$ simultaneously or independently are selected from the group consisting of $C_{1-6}$alkyl, $C_{2-6}$alkenyl and aryl;
- x and y simultaneously or independently are integers selected from the group consisting of 0, 1, 2, 3, and 4;
- n is an integer selected from the group consisting of 1, 2, 3 and 4; and
- X simultaneously or independently are $CH_2$, O, NH or $NR^c$.

28. The process according to claim 27, wherein $P_2NH$ is a compound of formula III(a) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3 and $R^{12}$ is $R^c$, in which $R^c$ is selected from the group consisting of $C_{1-6}$alkyl, $C_{2-6}$alkenyl and phenyl.

29. The process according to claim 28, wherein $P_2NH$ is a compound of formula III(a) and $R^7$ to $R^{10}$ simultaneously or independently are selected from the group consisting of H, methyl and phenyl, x and y simultaneously or independently are selected from the group consisting of 1 and 2, and $R^{12}$ is $R^c$, in which $R^c$ is selected from the group consisting of $C_{1-4}$alkyl and phenyl.

30. The process according to claim 29, wherein $R^7$ to $R^{10}$ are all H, x and y are both 1 and $R^c$ is selected from the group consisting of i-propyl and phenyl.

31. The process according to claim 27, wherein $P_2NH$ is a compound of formula III(b) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and n is 1 to 3.

32. The process according to claim 31, wherein $R^7$ to $R^{10}$ simultaneously or independently are selected from the group consisting of H, methyl and phenyl, x and y simultaneously or independently are selected from the group consisting of 1 and 2, $R^{13}$ is $R^c$, in which $R^c$ is methyl and n is 1 or 2.

33. The process according to claim 32, wherein $R^7$ to $R^{10}$ are all H, x and y are both 1 and n is 1.

34. The process according to claim 27, wherein $P_2NH$ is a compound of formula III(c) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl.

35. The process according to claim 34, wherein $R^7$ to $R^{10}$ simultaneously or independently are selected from the group consisting of H, methyl and phenyl, x and y simultaneously or independently are selected from the group consisting of 1 and 2, $R^{13}$ is $R^c$, in which $R^c$ is methyl and X is selected from the group consisting of $CH_2$, O and $NR^c$, in which $R^c$ is $C_{1-4}$alkyl.

36. The process according to claim 35, wherein $R^7$ to $R^{10}$ are all H, x and y are both 1 and X is selected from the group consisting of $CH_2$, O and NMe.

37. The process according to claim 27, wherein $P_2NH$ is a compound of formula III(d) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl.

38. The process according to claim 37, wherein $R^7$ to $R^{10}$ simultaneously or independently are selected from the group consisting of H, methyl and phenyl, x and y simultaneously or independently are selected from the group consisting of 1 and 2, $R^{13}$ is $R^c$, in which $R^c$ is methyl and X is selected from the group consisting of $CH_2$, O and $NR^c$, in which $R^c$ is $C_{1-4}$alkyl.

39. The process according to claim 38, wherein $R^7$ to $R^{10}$ are all H, x and y are both 1 and X is selected from the group consisting of $CH_2$, O and NMe.

40. The process according to claim 27, wherein $P_2NH$ is a compound of formula III(e) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl.

41. The process according to claim 40, wherein $R^7$ to $R^{10}$ simultaneously or independently are selected from the group consisting of H, methyl and phenyl, x and y simultaneously or independently are selected from the group consisting of 1 and 2, $R^{13}$ is $R^c$, in which $R^c$ is methyl and X is selected from the group consisting of $CH_2$, O and $NR^c$, in which $R^c$ is $C_{1-4}$alkyl.

42. The process according to claim 41, wherein $R^7$ to $R^{10}$ are all H, x and y are both 1 and X is selected from the group consisting of $CH_2$, O and NMe.

43. The process according to claim 27, wherein $P_2NH$ is a compound of formula III(f) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl.

44. The process according to claim 43, wherein $R^7$ to $R^{10}$ simultaneously or independently are selected from the group consisting of H, methyl and phenyl, x and y simultaneously or independently are selected from the group consisting of 1 and 2, $R^{13}$ is $R^c$, in which $R^c$ is methyl and X is selected from the group consisting of $CH_2$, O and $NR^c$, in which $R^c$ is $C_{1-4}$alkyl.

45. The process according to claim 44, wherein $R^7$ to $R^{10}$ are all H, x and y are both 1 and X is selected from the group consisting of $CH_2$, O and NMe.

46. The process according to claim 27, wherein $P_2NH$ is a compound of formula III(g) and $R^7$ to $R^{10}$ simultaneously or independently are selected from the group consisting of H, $C_{1-6}$alkyl, $C_{2-6}$alkenyl, $C_{3-6}$cycloalkyl and aryl, x and y simultaneously or independently are selected from the group consisting of 1, 2 and 3, $R^{13}$ is $R^c$, in which $R^c$ is $C_{1-6}$alkyl and X is selected from the group consisting of $CH_2$, O, NH and $NR^c$, in which $R^c$ is $C_{1-6}$alkyl.

47. The process according to claim 46, wherein $R^7$ to $R^{10}$ simultaneously or independently are selected from the group consisting of H, methyl and phenyl, x and y simultaneously or independently are selected from the group consisting of 1 and 2, $R^{13}$ is $R^c$, in which $R^c$ is methyl and X is selected from the group consisting of $CH_2$, O and $NR^c$, in which $R^c$ is $C_{1-4}$alkyl.

48. The process according to claim 47, wherein $R^7$ to $R^{10}$ are all H, x and y are both 1 and X is selected from the group consisting of $CH_2$, O and NMe.

49. The process according to claim 27, wherein $P_2NH$ is selected from a compound of the formula III(a), III(b) and III(f).

50. The process according to claim 1, wherein the metal complex is prepared and isolated prior to its use in the process or the metal complexes is prepared in situ, in the hydrogenation medium, without isolation or purification, just before its use.

51. The process according to claim 1, wherein the base in the transfer hydrogenation reaction, if used, is an organic non-coordinating base, an alkaline or alkaline-earth metal carbonate, a carboxylate salt or an alcoholate or hydroxide salt.

52. The process according to claim 40, wherein the base is an alcoholate or an hydroxide salt selected from the group consisting of compounds of formula $(R^{14}O)_2M'$ and $R^{14}OM''$, in which M' is an alkaline-earth metal, M" is an alkaline metal and $R^{14}$ is hydrogen or $C_{1-6}$alkyl.

53. The process according to claim 1, wherein primary and secondary alcohols are employed as the hydrogen donor.

54. The process according to claim 1, wherein carboxylic acids or their esters, are employed as the hydrogen donor.

55. The process according to claim 54, wherein at least some of the carboxylic acid is present as an amine salt or ammonium salt.

56. The process according to claim 55, wherein the tertiary amines is a trialkylamine.

57. The process according to claim 56, wherein the tertiary amine is triethylamine.

58. The process according to claim 1, wherein the transfer hydrogenation is carried out in a primary or secondary alcohol as solvent.

59. The process according to claim 1, wherein the solvent is selected from benzene, toluene, xylene, hexane, cyclohexane, tetrahydrofuran, and primary or secondary alcohols, and mixtures thereof.

60. The process according to claim 1, wherein the solvent is a primary, secondary or tertiary amine.

61. The process according to claim 1, wherein 2-propanol or 2-butanol is used as the hydrogen donor.

62. The process according to claim 1, wherein formic acid or triethylammonium formate is used as the hydrogen donor.

63. The process according to claim 1, wherein the transfer hydrogenation reaction is carried out in the presence of hydrogen gas.

64. The process according to claim 1, wherein the transfer hydrogenation procedure is carried out in the presence of an inert gas, such as nitrogen or argon, or in the presence of air.

* * * * *